United States Patent [19]

Kondo et al.

[11] Patent Number: 4,971,967
[45] Date of Patent: Nov. 20, 1990

[54] QUINOLINECARBOXYLIC ACID DERIVATIVES, ANTIBACTERIAL COMPOSITIONS AND USE

[75] Inventors: Hirosato Kondo, Suita; Masahiro Taguchi, Hirakata; Yoshimasa Inoue, Osaka; Fumio Sakamoto, Daito, all of Japan

[73] Assignee: Kanebo Ltd, Tokyo, Japan

[21] Appl. No.: 493,455

[22] Filed: Mar. 14, 1990

[30] Foreign Application Priority Data

Mar. 15, 1989 [JP] Japan .................................. 1-64617
Nov. 8, 1989 [JP] Japan .................................. 1-290406

[51] Int. Cl.$^5$ ................. A61K 31/495; A61K 31/535; C07D 513/06
[52] U.S. Cl. ................................. 514/233.2; 514/250; 544/115; 544/343
[58] Field of Search ............................. 544/115, 343; 514/233.2, 250

[56] References Cited

U.S. PATENT DOCUMENTS 4,853,469  8/1989  Taguchi et al. ...................... 544/99

Primary Examiner—Robert W. Ramsuer
Attorney, Agent, or Firm—Wegner & Bretschneider

[57] ABSTRACT

Novel quinolinecarboxylic acid derivatives of the formula:

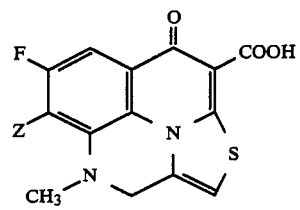

wherein Z is

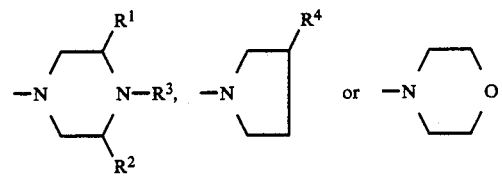

in which $R^1$ and $R^2$ are each hydrogen atom or a lower alkyl, $R^3$ is hydrogen atom, hydroxy or a lower alkyl and $R^4$ is hydrogen atom, hydroxy, amino, aminomethyl, a (lower alkyl)aminomethyl or a di(lower alkyl)aminomethyl, and a pharmaceutically acceptable salt thereof. The compounds have excellent antibacterial activities and are useful as an antibacterial agent.

6 Claims, No Drawings

QUINOLINECARBOXYLIC ACID DERIVATIVES, ANTIBACTERIAL COMPOSITIONS AND USE

The present invention relates to novel quinolinecarboxylic acid derivatives, an antibacterial agent containing said compounds as an active ingredient, a process for preparing said compounds and novel intermediate compound used for preparing said compounds. More particularly, the present invention relates to novel quinolinecarboxylic acid derivatives represented by the following formula (I):

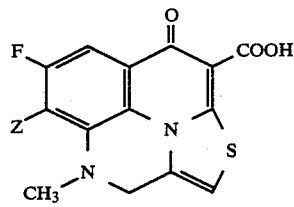

wherein Z is

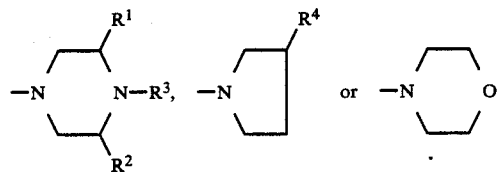

in which $R^1$ and $R^2$ are each hydrogen atom or a lower alkyl, $R^3$ is hydrogen atom, hydroxy or a lower alkyl and $R^4$ is hydrogen atom, hydroxy, amino, aminomethyl, a (lower alkyl)aminomethyl or a di(lower alkyl)aminomethyl and a pharmaceutically acceptable salt thereof, an antibacterial agent containing said compound (I) as an active ingredient, a process for preparing said compound (I) and novel intermediate compound used for preparing said compound (I).

PRIOR ART

Since the finding of nalidixic acid as a synthetic antibacterial agent, various quinolinecarboxylic acid derivatives including condensed tricyclic compounds and condensed tetracyclic compounds have hitherto been examined aiming at the improvement of an antibacterial activity. For example, U.S. Pat. No. 4,382,892 discloses condensed tricyclic compounds having a pyrido[1,2,3-de][1,4]benzoxazine ring including the following compound (X)(ofloxacin), and European Patent Publication No. 286089 (corresponding to U.S. Pat. No. 4,808,584, divisional application thereof U.S. Pat. No. 4,853,469) discloses condensed tetracyclic compounds having 9,1-epoxymethano-5H-thiazolo[3,2-a]quinoline ring including the following compound (Y).

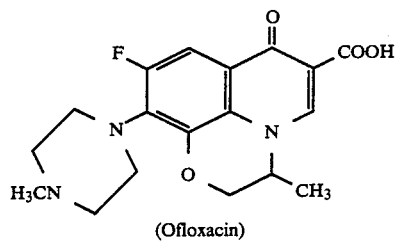

(Ofloxacin)

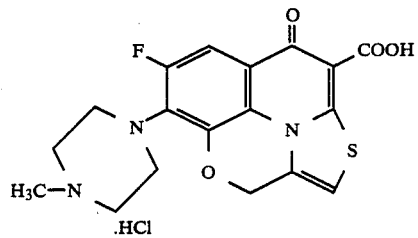

However, the above publications do not disclose the condensed tetracyclic compounds (I) of the present invention having a 9,1-iminomethano-5H-thiazolo[3,2-a]quinoline ring.

BRIEF SUMMARY OF THE INVENTION

The present inventors have studied to find novel quinolinecarboxylic acid derivatives having improved antibacterial activities and found that the novel quinolinecarboxylic acid derivatives having condensed tetracyclic ring of the formula (I) as described hereinbefore have improved antibacterial activities and are useful as an antibacterial agent.

An object of the present invention is to provide novel quinolinecarboxylic acid derivatives having a condensed tetracyclic ring which show improved antibacterial activities. Another object of the present invention is to provide an excellent antibacterial agent containing said compounds as an active ingredient. Still another object of the present invention is to provide a process for preparing said compounds. A further object of the present invention is to provide novel intermediate compounds used for preparing said compounds.

DETAILED DESCRIPTION OF THE INVENTION

The quinolinecarboxylic acid derivatives of the present invention are 9,1-iminomethano-5H-thiazolo[3,2-a]quinoline-4-carboxylic acid derivatives of the formula (I) as described hereinbefore and a pharmaceutically acceptable salt thereof, which show potent antibacterial activities with a wider antibacterial spectrum.

Through the present specification and claims, the term "lower alkyl" denotes a straight chain or branched chain alkyl having 1 to 4 carbon atoms, such as methyl, ethyl, n-propyl, isopropyl, n-butyl, sec-butyl, tert-butyl, and the like.

Suitable examples of the above cyclic amino group (Z) are 1-piperazinyl, 4-methyl-1-piperazinyl, 4-ethyl-1-piperazinyl, 3,5-dimethyl-1-piperazinyl, 3-methyl-1-piperazinyl, 3,4-dimethyl-1-piperazinyl, 3,4,5-trimethyl-1-piperazinyl, 4-hydroxy-1-piperazinyl, 1-pyrrolidinyl, 3-hydroxy-1-pyrrolidinyl, 3-amino-1-pyrrolidinyl, 3-aminomethyl-1-pyrrolidinyl, 3-methylaminomethyl-1-pyrrolidinyl, 3-dimethylaminomethyl-1-pyrrolidinyl, 3-ethylaminomethyl-1-pyrrolidinyl, morpholino, and the like.

Preferred compounds of the invention are quinolinecarboxylic acid derivatives of the formula (I) wherein Z is

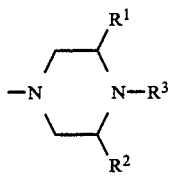

(where $R^1$ and $R^2$ are each hydrogen atom or $C_{1-2}$ alkyl, and $R^3$ is hydrogen atom, hydroxy or a $C_{1-2}$ alkyl),

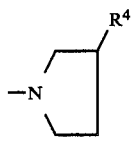

(where $R^4$ is hydrogen atom, hydroxy, amino, a ($C_{1-2}$ alkyl)aminomethyl or a di($C_{1-2}$ alkyl)aminomethyl), or

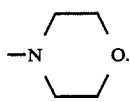

More preferred compounds are the compounds of the formula (I) wherein Z is

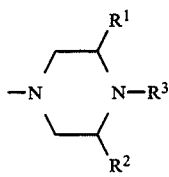

(where $R^1$ and $R^2$ are each hydrogen atom or methyl, and $R^3$ is hydrogen atom, hydroxy, methyl or ethyl),

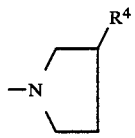

(where $R^4$ is hydrogen atom, hydroxy, amino, methylaminomethyl, or ethylaminomethyl), or

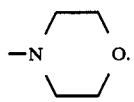

Particularly preferred compounds are the compounds of the formula (I) wherein Z is 1-piperazinyl, 4-methyl-1-piperazinyl, 4-ethyl-1-piperazinyl, 3,5-dimethyl-1-piperazinyl, 3-methyl-1-piperazinyl, 3,4-dimethyl-1-piperazinyl, 3,4,5-trimethyl-1-piperazinyl, 4-hydroxy-1-piperazinyl, 1-pyrrolidinyl, 3-hydroxy-1-pyrrolidinyl, 3-amino-1-pyrrolidinyl, 3-aminomethyl-1-pyrrolidinyl, 3-methylaminomethyl-1-pyrrolidinyl, 3-dimethylaminomethyl-1-pyrrolidinyl, 3-ethylaminomethyl-1-pyrrolidinyl, or morpholino.

The compounds of the present invention include a pharmaceutically acceptable salt of the compound of the formula (I). Preferred pharmaceutically acceptable salt of the compound (I) of the present invention are metallic salts such as sodium salt, potassium salt and calcium salt, an ammonium salt and basic amino acid salts such as salts with lysine and arginine at the carboxyl group; and where Z is

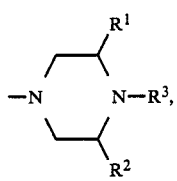

in which $R^1$, $R^2$ and $R^3$ are as defined above, or pyrrolidinyl having amino, aminomethyl, a (lower alkyl)aminomethyl or a di(lower alkyl)aminomethyl, addition salts of inorganic acids such as hydrochloric acid and sulfuric acid, and of organic acids such as maleic acid, fumaric acid, tartaric acid, methanesulfonic acid and p-toluenesulfonic acid are also included.

The compounds of the present invention (I) or a salt thereof can be prepared by, for example, any of the following three processes (A), (B) and (C) utilizing novel intermediate compounds of the present invention represented by the formula (II):

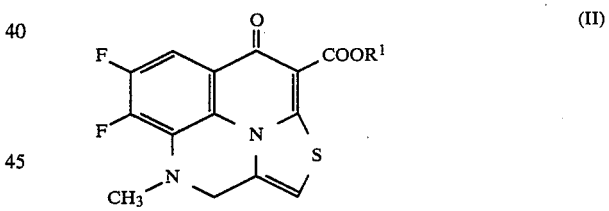

wherein $R^1$ is as defined above. In the following description, the compound of the formula (II) wherein $R^1$ is hydrogen atom is designated (II-1) and those wherein $R^1$ is a lower alkyl are designated (II-2).

The compounds of the formula (I) of the present invention can be prepared by the following process (A).

Process (A)

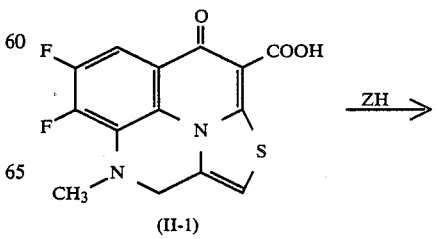

-continued

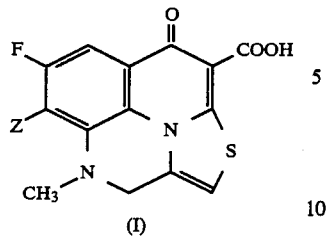

wherein Z is as defined above.

The compounds (I) of the present invention can be prepared by reacting a compound (II-1), which is a compound (II) wherein $R^1$ is hydrogen atom, with a cyclic amine (ZH) or an acid addition salt thereof in a polar organic solvent such as dimethyl sulfoxide or N,N-dimethylformamide in the presence of an acid scavenger.

The acid scavenger includes a tertiary amine such as triethylamine or an inorganic base such as sodium carbonate or potassium carbonate. An excess amount of the above cyclic amine (ZH) can also be employed as the acid scavenger. When the acid scavenger is the excess cyclic amine (ZH), one mole of the compound (II-1) is usually reacted with 3 to 7 moles of the cyclic amine (ZH). In the case that the tertiary amine or the inorganic base is employed as the acid scavenger, the reaction is usually carried out in such a way that one mole of the compound (II-1) is reacted with 1 to 1.5 moles of the cyclic amine (ZH) or the acid addition salt thereof employing 2 to 6 moles of the acid scavenger.

The reaction temperature ranges from 30° to 150° C., preferably from 50° to 120° C. The reaction is usually carried out for about 30 minutes to about 50 hours though it may vary depending on the kind of the cyclic amine (ZH) and the reaction temperature.

The compounds (I) of the present invention can also be prepared by the following process (B).

Process (B)

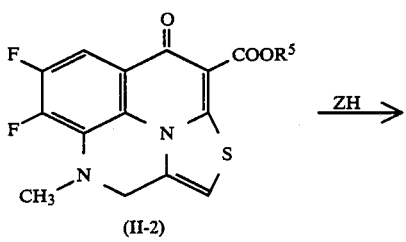

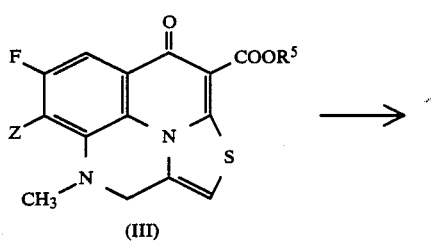

wherein Z is as defined above and $R^5$ is a lower alkyl.

That is, a compound (II-2), which is the compound (II) wherein $R^1$ is a lower alkyl, is reacted, as in the above process (A), with the cyclic amine (ZH) or an acid addition salt thereof in a polar organic solvent such as dimethyl sulfoxide or N,N-dimethylformamide in the presence of an acid scavenger for 5 to 85 hours to give a compound of the formula (III), and hydrolyzing the obtained compound (III) in the conventional manner to give the compound (I) of the present invention.

The acid scavenger employed in the above process (B) is the same as those employed in the process (A). The reaction temperature is also the same as that of the process (A).

Further, the compounds (I) of the present invention can also be prepared by the following process (C).

Process (C)

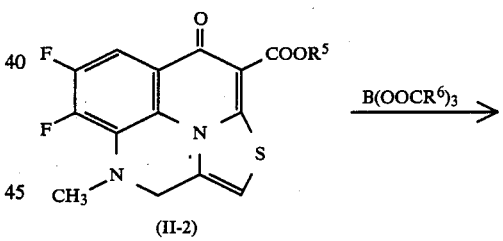

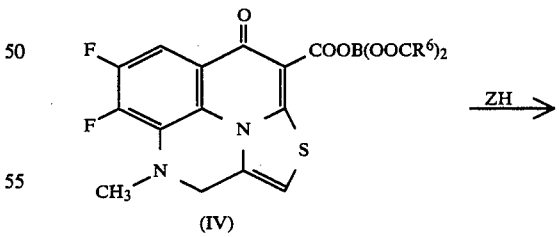

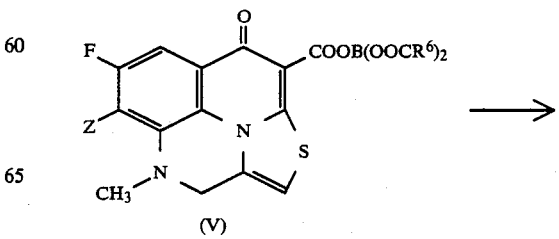

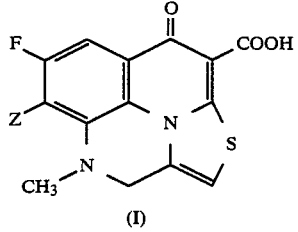

(I)

wherein $R^5$ and Z are as defined above and $R^6$ is a lower alkyl.

That is, a compound (II-2), which is the compound (II) wherein $R^1$ is a lower alkyl, is reacted with a tri(-lower alkylcarboxy)borane in a (lower alkyl)carboxylic acid anhydride to give the compound (IV). The compound (IV) is then reacted with a cyclic amine (ZH) or an acid addition salt thereof in a polar solvent such as dimethyl sulfoxide or N,N-dimethylformamide in the presence of an acid scavenger usually at room temperature to 100° C. for 1 to 30 hours to give the compound (V). The acid scavenger used in this reaction includes tertiary amines such as triethylamine or an excess amount of the above cyclic amine (ZH). Finally, the compound (V) is hydrolyzed under acidic conditions, preferably under acidic conditions with hydrochloric acid, to prepare a compound (I) of the present invention or an acid addition salt thereof. Among the compounds (I) of the present invention, a compound of the formula (I'), which is a compound (I) wherein Z is 3-amino-1-pyrrolidinyl or 3-aminomethyl-1-pyrrolidinyl, can also prepared by the following reaction.

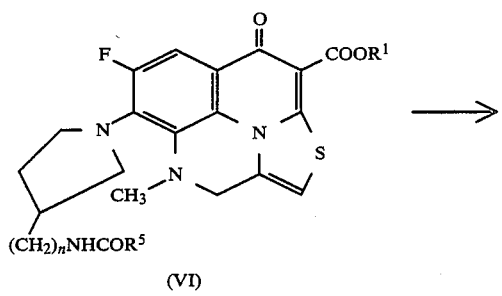

(VI)

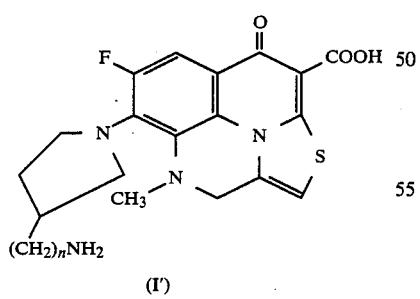

(I')

wherein $R^1$ and $R^5$ are as defined above and n is an integer of 0 or 1.

That is, a compound (VI), which is prepared by reacting the compound (II) with 3-acylaminopyrrolidine or 3-(acylaminomethyl)pyrrolidine in accordance with the process (A), is hydrolyzed in the conventional manner, preferably with an alkali, to give the compound (I') of the present invention.

The compounds (I) of the present invention wherein Z is

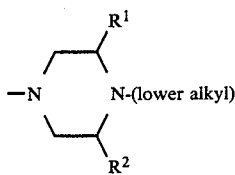

wherein $R^1$ and $R^2$ are as defined above can also be prepared by reacting the compound (I) of the present invention wherein Z is

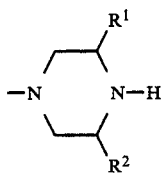

wherein $R^1$ and $R^2$ are as defined above with a lower alkyl halide in a polar solvent such as N,N-dimethylformamide in the presence of an acid scavenger such as potassium carbonate, and optionally hydrolyzing side products with an alkali.

The compounds (I) of the present invention wherein Z is

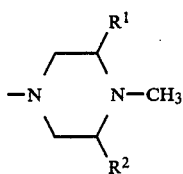

wherein $R^1$ and $R^2$ are as defined above can be prepared by reacting the compound (I) of the present invention wherein Z is

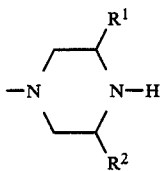

wherein $R^1$ and $R^2$ are as defined above with formalin and formic acid to produced a reductive methylation reaction.

The compounds (I) of the present invention thus prepared by the above processes, or an acid addition salt thereof, can be isolated and purified by the conventional procedure, for example, silica-gel column chromatography or recyrstallization. The compounds (I) of the present invention can also be converted into pharmaceutically acceptable salt thereof by the conventional procedure.

The intermediate compounds (II) used in the above processes (A) to (C) for preparing the compound (I) of the present invention are novel compounds and prepared by any of the following three processes (a), (b) and (c).

Process (a)

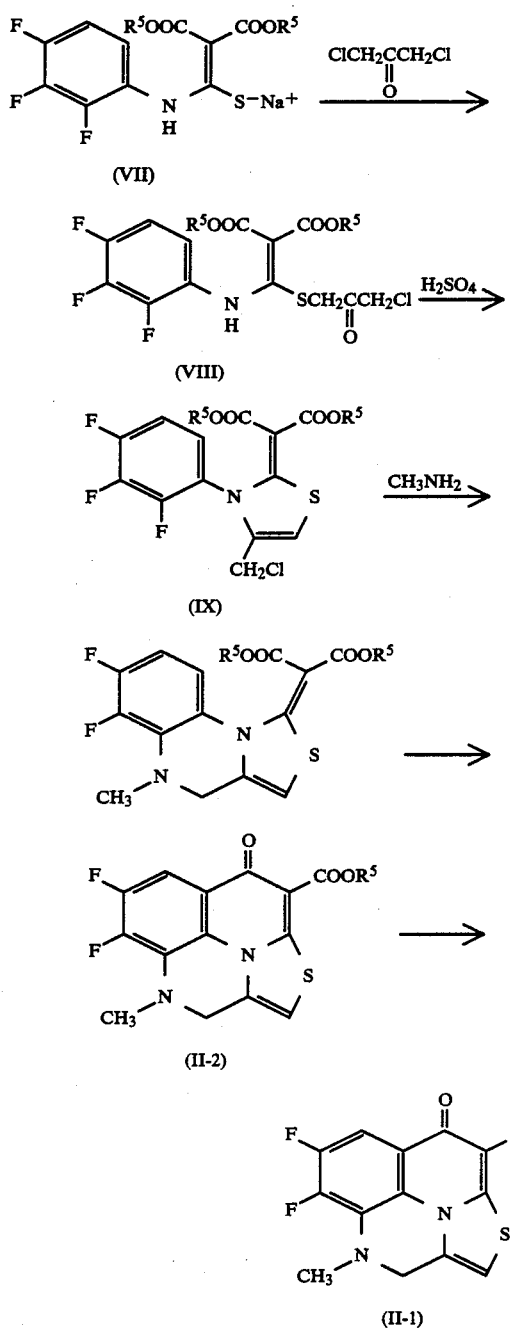

wherein $R^5$ is as defined above.

That is, first the compound (VII) (see European patent publication No. 286089) is reacted with 1,3-dichloroacetone in a polar organic solvent such as N,N-dimethylformamide, dimethyl sulfoxide or acetonitrile to produce di(lower alkyl) [(2,3,4-trifluoroanilino)(3-chloro-2-oxopropylthio)methylene]malonate (VIII). The compound (VIII) is then reacted with sulfuric acid to give di(lower alkyl) [3-(2,3,4-trifluorophenyl)-4-chloromethyl-3H-thiazol-2-ylidene]malonate (IX). The compound (IX) is then reacted with methylamine in an organic solvent such as acetonitrile or N,N-dimethylformamide to give di(lower alkyl) (1H,4H-thiazolo[3,4-a]quinoxalin-1-ylidene)malonate (X). The compound (X) is heated with a condensing agent such as polyphosphoric acid or polyphosphoric acid ethyl ester to cyclize the compound (X) to produce the compound (II-2) which is the compound (II) wherein $R^1$ is a lower alkyl. Finally, the compound (II-2) is hydrolyzed with heating in conc. sulfuric acid at 60° to 100° C. to give the compound (II-1) which is the compound (II) wherein $R^1$ is hydrogen atom. Alternatively, the compound (II-2) is reacted with a tri(lower alkylcarboxy)borane in a (lower alkyl)carboxylic acid anhydride to give the above compound (IV) and then the compound (IV) is hydrolyzed under acidic conditions to give the compound (II-1). The compound (II-1) can also be prepared by reacting the compound (X) with fuming sulfuric acid at around room temperature.

The intermediate compound (II) of the present invention can also be prepared by the following process (b).

Process (b)

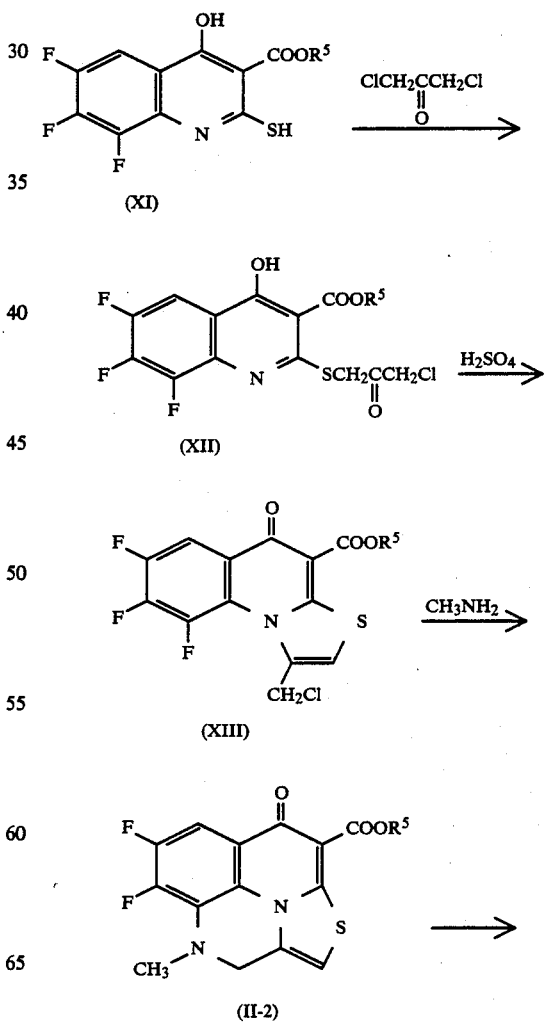

-continued

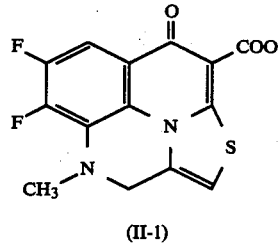

(II-1)

wherein $R^5$ is as defined above.

That is, first the known compound (XI)(see European patent publication No. 286089) is reacted with 1,3-dichloroacetone in a solvent of a halogenated compound such as chloroform or methylene chloride in the presence of a tertiary amine such as triethylamine to produce lower alkyl 2-(3-chloro-2-oxopropylthio)-6,7,8-trifluoro-4-hydroxy-quinoline-3-carboxylate (XII). The compound (XII) is then reacted with sulfuric acid to give lower alkyl 7,8,9-trifluoro-1-chloromethyl-5-oxo-5H-thiazolo[3,2-a]quinoline-4-carboxylate (XIII). The compound (XIII) is then reacted with methylamine in an organic solvent such as acetonitrile or N,N-dimethylformamide to give the compound (II-2) which is the compound (II) wherein $R^1$ is a lower alkyl. The compound (II-1) which is the compound (II) wherein $R^1$ is hydrogen atom can be prepared from the compound (II-2) in the same manner as in the above process (a).

Alternatively, the intermediate compounds (II) of the present invention can be prepared by the following process (c).

Process (c)

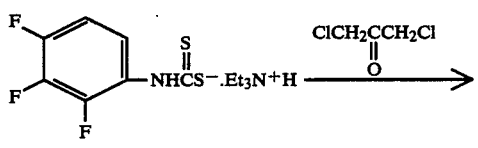

(XIV)

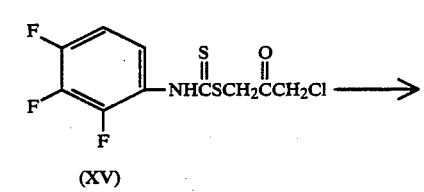

(XV)

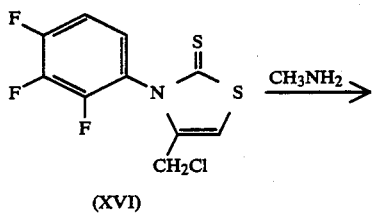

(XVI)

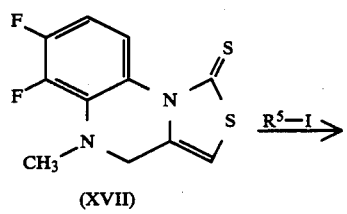

(XVII)

-continued

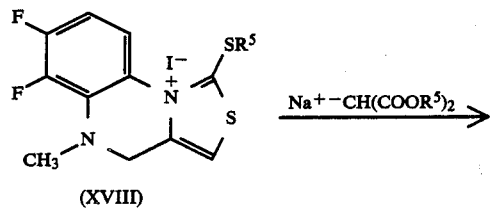

(XVIII)

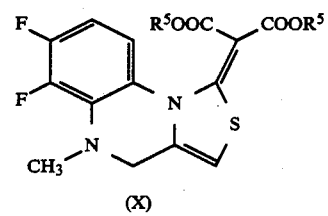

(X)

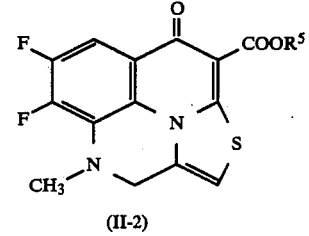

(II-2)

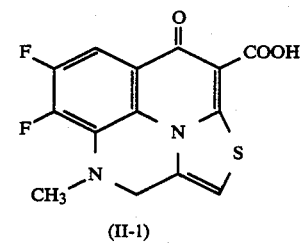

(II-1)

wherein $R^5$ is as defined above.

That is, first the known compound (XIV)(see European patent publication No. 286089) is reacted with 1,3-dichloroacetone in an organic solvent such as chloroform, methylene chloride or a lower alcohol to produce 3-chloro-2-oxopropyl N-(2,3,4-trifluorophenyl)dithiocarbamate (XV). The compound (XV) is then heated with an inorganic acid such as hydrochloric acid or sulfuric acid in a lower alcohol such as ethanol to give 4-chloromethyl-3-(2,3,4-trifluorophenyl)-2(3H)-1,3-thiazolethione (XVI). The compound (XVI) is then reacted with methylamine in an aprotic organic solvent such as N,N-dimethylformamide or acetonitrile to give 1H,4H-thiazolo[3,4-a]quinoxaline-1-thione derivative (XVII). The compound (XVII) is then reacted with a lower alkyl iodide in a polar solvent such as N,N-dimethylformamide, acetonitrile or ethanol to give a 1-(lower alkyl)thioquinoxalino[1,2-c]thiazolium iodide (XVIII). Then the compound (XVIII) is reacted with a di(lower alkyl) malonate sodium, which is prepared from di(lower alkyl) malonate and sodium hydride, in an organic solvent such as tetrahydrofuran or dioxane to give di(lower alkyl) (1H,4H-thiazolo[3,4-a]quinoxalin-1-ylidene)malonate (X).

Alternatively, the compound (X) can also be prepared by reacting the compound (XVII) with phosgene or trichloromethyl chloroformate in an inert solvent such as toluene or benzene and then reacting the obtained product with a di(lower alkyl) malonate in a polar solvent such as acetonitrile in the presence of a tertiary amine such as triethylamine.

The compound (X) is subsequently treated in the same manner as in the process (a) to give the compounds (II-1) and (II-2).

The compounds (I) of the present invention and pharmaceutically acceptable salts thereof show excellent antibacterial activities with a low toxicity as shown hereinbelow and are useful as an antibacterial agent.

When the compounds (I) of the present invention and pharmaceutically acceptable salts thereof are used for an antibacterial agent, they are administered to the human by oral route or parenterally such as by injection. The dosage form for oral administration includes solid preparations such as tablets, granules, powders, fine granules and hard capsules as well as liquid preparations such as syrups and soft capsules. The pharmaceutical preparations can be prepared by the conventional procedure. Tablets, granuls, powders and fine granules are prepared by mixing the compound (I) of the present invention or a pharmaceutically acceptable salt thereof with conventional pharmaceutically acceptable nontoxic carriers such as lactose, starch, crystalline cellulose, magnesium stearate, hydroxypropyl cellulose, talc, and the like. Hard capsules are prepared by packing the above fine granules or powders into capsules. Syrups are prepared by dissolving or suspending the compound (I) of the present invention or a pharmaceutically acceptable salt thereof in an aqueous solution containing white sugar, carboxymethyl cellulose and the like. Soft capsules are prepared by dissolving or suspending the compound (I) of the present invention or a pharmaceutically acceptable salt thereof in fatty diluents such as vegetable oils, oil emulsions and glycols and packing the solution or suspension into soft capsules.

Injections are prepared by dissolving or suspending the compound (I) of the present invention or a pharmaceutically acceptable salt thereof in physiological saline or in fatty diluents such as vegetable oils, oil emulsions and glycols and aseptically packing the solution or emulsion in ampoules or vials.

The dose of the compound (I) of the present invention, though it may vary depending on an age or a body weight of patients or severity of diseases, is generally in the range of from 0.5 to 30 mg/kg of body weight/day, preferably from 2 to 20 mg/kg of body weight/day [as the compound (I)], which may be administered once a day or may divided into 2 to 4 times per day.

The compounds (I) of the present invention and pharmaceutically acceptable salts thereof have a wider antibacterial spectrum and potent antibacterial activities as shown in the following Experiment 1. The compounds (I) of the present invention and pharmaceutically acceptable salts thereof show particularly strong antibacterial activities against Gram positive bacteria and also show strong antibacterial activities against methicillin resistant Staphylococcus aureus clinically isolated as demonstrated in the following Experiment 2. Further, tests employing experimental animals prove that the compounds (I) of the present invention and pharmaceutically acceptable salts thereof, e.g. the compounds prepared in Examples 7-(a), 15, 24 and 25, showed excellent protective effects against infection as seen in the following Experiments 3 and 4 and had low toxicity as demonstrated in the following Experiments 5 and 6. Consequently, it is clear that the compounds (I) of the present invention and pharmaceutically acceptable salts thereof are useful as an excellent agent for the prophylaxis and treatment of infectious diseases.

The antibacterial activities of the compounds (I) of the present invention and pharmaceutically acceptable salts thereof were tested in the following Experiments.

Experiment 1 Antibacterial activities (Minimum inhibitory concentration :MIC)

1. Test compounds:

The following compounds of the present invention were tested for antibacterial activities. The known compounds (X) and (Y) as mentioned above were also tested as reference.

Compound (A): 9,1-(Methylimino)methano-7-fluoro-8-(4-methyl-1-piperazinyl)-5-oxo-5H-thiazolo[3,2-a]quinoline-4-carboxylic acid [compound of Example 7-(a)]

Compound (B): 9,1-(Methylimino)methano-7-fluoro-8-(4-methyl-1-piperazinyl)-5-oxo-5H-thiazolo [3,2-a]quinoline-4-carboxylic acid hydrochloride [compound of Example 7-(b)]

Compound (C): 9,1-(Methylimino)methano-7-fluoro-8-(1-piperazinyl)-5-oxo-5H-thiazolo[3,2-a]quinoline-4-carboxylic acid [compound of Example 8]

Compound (D): 9,1-(Methylimino)methano-7-fluoro-8-(3-methyl-1-piperazinyl)-5-oxo-5H-thiazolo[3,2-a]quinoline-4-carboxylic acid [compound of Example 9]

Compound (E): 9,1-(Methylimino)methano-7-fluoro-8-(3,5-dimethyl-1-piperazinyl)-5-oxo-5H-thiazolo[3,2-a]-quinoline-4-carboxylic acid [compound of Example 10]

Compound (F): 9,1-(Methylimino)methano-7-fluoro-8-(1-pyrrolidinyl)-5-oxo-5H-thiazolo[3,2-a]quinoline-4-carboxylic acid [compound of Example 11]

Compound (G): 9,1-(Methylimino)methano-7-fluoro-8-(3-hydroxy-1-pyrrolidinyl)-5-oxo-5H-thiazolo[3,2-a]quinoline-4-carboxylic acid [compound of Example 12]

Comound (H): 9,1-(Methylimino)methano-7-fluoro-8-(3-amino-1-pyrrolidinyl)-5-oxo-5H-thiazolo[3,2-a]quinoline-4-carboxylic acid [compound of Example 13]

Compound (I): 9,1-(Methylimino)methano-7-fluoro-8-morpholino-5-oxo-5H-thiazolo[3,2-a]quinoline-4-carboxylic acid [compound of Example 14]

Compound (J): 9,1-(Methylimino)methano-7-fluoro-8-(4-ethyl-1-piperazinyl)-5-oxo-5H-thiazolo[3,2-a]quinoline-4-carboxylic acid [compound of Example 15]

Compound (K): 9,1-(Methylimino)methano-7-fluoro-8-(4-ethyl-1-piperazinyl)-5-oxo-5H-thiazolo[3,2-a]quinoline-4-carboxylic acid hydrochloride [compound of Example 19]

Compound (L): 9,1-(Methylimino)methano-7-fluoro-8-(4-hydroxy-1-piperazinyl)-5-oxo-5H-thiazolo[3,2-a]quinoline-4-carboxylic acid [compound of Example 16]

Compound (M): 9,1-(Methylimino)methano-7-fluoro-8-(3-ethylaminomethyl-1-pyrrolidinyl)-5-oxo-5H-thiazolo[3,2-a]quinoline-4-carboxylic acid hydrochloride [compound of Example 17]

Compound (N): 9,1-(Methylimino)methano-7-fluoro-8-(3-methylaminomethyl-1-pyrrolidinyl)-5-oxo-5H-thiazolo[3,2-a]quinoline-4-carboxylic acid hydrochloride [compound of Example 18]

Compound (O): 9,1-(Methylimino)methano-7-fluoro-8-(3,4-dimethyl-1-piperazinyl)-5-oxo-5H-thiazolo[3,2-a]quinoline-4-carboxylic acid [compound of Example 24]

Compound (P): 9,1-(Methylimino)methano-7-fluoro-8-(3,4,5-trimethyl-1-piperazinyl)-5-oxo-5H-thiazolo[3,2-a]quinoline-4-carboxylic acid [compound of Example 25]

Compound (X): 9-Fluoro-3-methyl-10-(4-methyl-1-piperazinyl)-7-oxo-2,3-dihydro-7H-pyrido[1,2,3-de][1,4]-benzoxazine-6-carboxylic acid (reference compound disclosed in U.S. Pat. No. 4,382,892)

Compound (Y): 9,1-Epoxymethano-7-fluoro-8-(4-methyl-1-piperazinyl)-5-oxo-5H-thiazolo[3,2-a]quinoline-4-carboxylic acid hydrochloride (reference compound disclosed in European Patent Publication No. 286089)

2. Method:

The compounds of the present invention (A, C, D, E, F, G, H, I, J, L, O and P) and the known compound (X) as reference were dissolved in 0.1 N aqueous sodium hydroxide to prepare a solution of 5000 μg/ml in concentration. The compounds of the present invention (B, K, M and N) and the known compound (Y) were dissolved in sterilized distilled water to prepare a solution of 5000 μg/ml in concentration. Each solution was diluted with sterilized distilled water to prepare a standard solution with a concentration of each test compound: 1000 μg/ml. The test was carried out by a method as appointed by Japan Society of Chemotherapy [cf. Chemotherapy, 29, 76–79 (1981)(TOKYO)].

3. Results:

The test results are shown in Tables 1-1 and 1-2.

TABLE 1-1

| Microorganisms | Gram | Minimum inhibitory concentration (MIC: μg/ml) Compounds of the present invention |||||||||
|---|---|---|---|---|---|---|---|---|---|---|
| | | A | B | C | D | E | F | G | H | I |
| Staphylococcus aureus FDA 209P JC-1 | + | 0.05 | 0.05 | 0.05 | 0.05 | 0.05 | 0.0125 | 0.0125 | 0.025 | 0.006 |
| Staphylococcus aureus IID 803 | + | 0.05 | 0.05 | 0.05 | 0.05 | 0.05 | 0.0125 | 0.0125 | 0.006 | 0.006 |
| Staphylococcus epidermidis IAM-1296 | + | 0.05 | 0.10 | 0.05 | 0.05 | 0.10 | 0.025 | 0.0125 | 0.05 | 0.025 |
| Streptococcus faecalis IID 682 | + | 0.10 | 0.10 | 0.05 | 0.10 | 0.20 | 0.10 | 0.05 | 0.05 | 0.05 |
| Bacillus subtilis ATCC 6633 | + | 0.006 | 0.025 | 0.006 | 0.006 | 0.025 | 0.006 | 0.006 | 0.006 | 0.006 |
| Micrococcus luteus ATCC 9341 | + | 0.39 | 0.39 | 0.39 | 0.39 | 0.39 | 0.39 | 0.39 | 0.20 | 0.10 |
| Escherichia coli NIHJ JC-2 | − | 0.05 | 0.05 | 0.05 | 0.05 | 0.10 | 0.20 | 0.10 | 0.05 | 0.10 |
| Escherichia coli KC-14 | − | 0.05 | 0.05 | 0.05 | 0.05 | 0.05 | 0.20 | 0.10 | 0.0125 | 0.10 |
| Klebsiella pneumoniae PCI-602 | − | 0.006 | 0.006 | 0.006 | 0.006 | 0.006 | 0.006 | 0.006 | 0.006 | 0.006 |
| Salmonella typhimurium IID 971 | − | 0.05 | 0.05 | 0.05 | 0.05 | 0.10 | 0.20 | 0.05 | 0.05 | 0.05 |
| Shigella sonnei EW-33 | − | 0.025 | 0.05 | 0.025 | 0.05 | 0.05 | 0.10 | 0.05 | 0.05 | 0.05 |
| Serratia marcescens IAM 1184 | − | 0.20 | 0.39 | 0.20 | 0.39 | 0.78 | 0.78 | 0.78 | 0.10 | 0.39 |
| Pseudomonas aeruginosa IFO 3445 | − | 0.39 | 0.78 | 0.39 | 0.78 | 1.56 | 0.78 | 0.78 | 0.20 | 0.39 |
| Pseudomonas aeruginosa NCTC 10490 | − | 0.20 | 0.39 | 0.20 | 0.39 | 0.39 | 0.39 | 0.39 | 0.20 | 0.20 |
| Pseudomonas aeruginosa E-2 | − | 0.78 | 0.78 | 0.39 | 0.78 | 1.56 | 0.39 | 0.78 | 0.39 | 0.39 |
| Morganella morganii IFO 3848 | − | 0.05 | 0.10 | 0.05 | 0.10 | 0.39 | 0.39 | 0.20 | 0.05 | 0.10 |
| Proteus vulgaris OX-19 | − | 0.0125 | 0.0125 | 0.006 | 0.006 | 0.05 | 0.025 | 0.0125 | 0.0125 | 0.025 |
| Proteus mirabilis IFO 3849 | − | 0.20 | 0.20 | 0.10 | 0.20 | 0.78 | 0.39 | 0.10 | 0.10 | 0.10 |
| Enterobacter aerogenes ATCC 13048 | − | 0.05 | 0.05 | 0.05 | 0.05 | 0.20 | 0.39 | 0.20 | 0.05 | 0.20 |
| Enterobacter cloacae 963 | − | 0.05 | 0.10 | 0.05 | 0.05 | 0.20 | 0.39 | 0.20 | 0.05 | 0.10 |
| Citrobacter freundii NIHJ 10018-68 | − | 0.20 | 0.39 | 0.10 | 0.39 | 1.56 | 1.56 | 0.78 | 0.10 | 0.78 |
| Acinetobacter calcoaceticus AC 54 | − | 0.025 | 0.05 | 0.025 | 0.025 | 0.025 | 0.006 | 0.006 | 0.0125 | 0.006 |

TABLE 1-2

| Microoganisms | Gram | Minimum inhibitory concentration (MIC: μg/ml) |||||||| |
|---|---|---|---|---|---|---|---|---|---|---|
| | | Compounds of the present invention |||||||| Known comp. |
| | | J | K | L | M | N | O | P | X | Y |
| Staphylococcus aureus FDA 209P JC-1 | + | 0.05 | 0.05 | 0.05 | 0.025 | 0.025 | 0.025 | 0.025 | 0.39 | 0.20 |
| Staphylococcus aureus IID 803 | + | 0.05 | 0.05 | 0.05 | 0.0125 | 0.0125 | 0.025 | 0.025 | 0.39 | 0.20 |
| Staphylococcus | + | 0.10 | 0.10 | 0.10 | 0.05 | 0.05 | 0.05 | 0.10 | 0.78 | 0.39 |

TABLE 1-2-continued

| Microorganisms | Gram | Minimum inhibitory concentration (MIC: μg/ml) | | | | | | | | |
|---|---|---|---|---|---|---|---|---|---|---|
| | | Compounds of the present invention | | | | | | | Known comp. | |
| | | J | K | L | M | N | O | P | X | Y |
| epidermidis IAM-1296 | | | | | | | | | | |
| Streptococcus faecalis IID 682 | + | 0.10 | 0.20 | 0.10 | 0.05 | 0.05 | 0.10 | 0.20 | 1.56 | 0.78 |
| Bacillus subtilis ATCC 6633 | + | 0.025 | 0.025 | 0.0125 | 0.0125 | 0.025 | 0.0125 | 0.006 | 0.10 | 0.10 |
| Micrococcus luteus ATCC 9341 | + | 0.39 | 0.39 | 0.78 | 0.20 | 0.20 | 0.39 | 0.39 | 3.13 | 1.56 |
| Escherichia coli NIHJ JC-2 | − | 0.10 | 0.10 | 0.10 | 0.10 | 0.10 | 0.05 | 0.10 | 0.10 | 0.10 |
| Escherichia coli KC-14 | − | 0.05 | 0.05 | 0.10 | 0.10 | 0.05 | 0.05 | 0.10 | 0.10 | 0.10 |
| Klebsiella pneumoniae PCI-602 | − | 0.006 | 0.006 | 0.006 | 0.006 | 0.0125 | 0.006 | 0.006 | 0.05 | 0.025 |
| Salmonella typhimurium IID 971 | − | 0.05 | 0.05 | 0.10 | 0.10 | 0.10 | 0.20 | 0.39 | 0.05 | 0.05 |
| Shigella sonnei EW-33 | − | 0.05 | 0.05 | 0.05 | 0.05 | 0.05 | 0.05 | 0.05 | 0.05 | 0.05 |
| Serratia marcescens IAM 1184 | − | 0.39 | 0.39 | 0.78 | 0.78 | 0.78 | 0.39 | 1.56 | 0.78 | 0.39 |
| Pseudomonas aeruginosa IFO 3445 | − | 0.78 | 0.78 | 0.78 | 1.56 | 0.78 | 1.56 | 3.13 | 1.56 | 1.56 |
| Pseudomonas aeruginosa NCTC 10490 | − | 0.39 | 0.39 | 0.39 | 0.39 | 0.39 | 0.78 | 1.56 | 1.56 | 0.78 |
| Pseudomonas aeruginosa E-2 | − | 0.78 | 0.78 | 0.78 | 1.56 | 0.78 | 0.78 | 1.56 | 1.56 | 0.78 |
| Morganella morganii IFO 3848 | − | 0.10 | 0.20 | 0.10 | 0.20 | 0.20 | 0.20 | 0.39 | 0.10 | 0.10 |
| Proteus vulgaris OX-19 | − | 0.025 | 0.025 | 0.0125 | 0.05 | 0.05 | 0.025 | 0.10 | 0.05 | 0.05 |
| Proteus mirabilis IFO 3849 | − | 0.39 | 0.39 | 0.20 | 0.39 | 0.39 | 0.39 | 0.78 | 0.39 | 0.20 |
| Enterobacter aerogenes ATCC 13048 | − | 0.10 | 0.10 | 0.10 | 0.10 | 0.20 | 0.10 | 0.20 | 0.10 | 0.10 |
| Enterobacter cloacae 963 | − | 0.10 | 0.10 | 0.10 | 0.20 | 0.10 | 0.10 | 0.20 | 0.20 | 0.10 |
| Citrobacter freundii NIHJ 10018-68 | − | 0.39 | 0.39 | 0.39 | 0.78 | 0.78 | 0.39 | 1.56 | 0.39 | 0.20 |
| Acinetobacter calcoaceticus Ac 54 | − | 0.05 | 0.05 | 0.025 | 0.05 | 0.05 | 0.025 | 0.025 | 0.39 | 0.20 |

Experiment 2 Minimum inhibitory concentration against clinically isolated methicillin resistant Staphylococcus aureus 1. Test compounds:

Compound (A): 9,1-(Methylimino)methano-7-fluoro-8-(4-methyl-1-piperazinyl)-5-oxo-5H-thiazolo[3,2-a]quinoline-4-carboxylic acid [compound of Example 7-(a)]

Compound (J): 9,1-(Methylimino)methano-7-fluoro-8-(4-ethyl-1-piperazinyl)-5-oxo-5H-thiazolo[3,2-a]quinoline-4-carboxylic acid [compound of Example 15]

Compound (X): 9-Fluoro-3-methyl-10-(4-methyl-1-piperazinyl)-7-oxo-2,3-dihydro-7H-pyrido[1,2,3-de][1,4-benzoxazine-6-carboxylic acid (reference compound disclosed in U.S. Pat. No. 4,382,892)

Compound (Y): 9,1-Epoxymethano-7-fluoro-8-(4-methyl-1-piperazinyl)-5-oxo-5H-thiazolo[3,2-a]quinoline-4-carboxylic acid hydrochloride (reference compound disclosed in European Patent Publication No. 286089)

2. Method:

The compounds (A) and (J) of the present invention and the known compound (X) were dissolved in 0.1 N aqueous sodium hydroxide, and the known compound (Y) in sterilized distilled water, to prepare a solution of 5000 μg/ml in concentration each. The above solutions were then diluted with sterilized distilled water to prepare a standard solution with a concentration of the test compound: 1000 μg/ml each. The test was carried out by a method appointed by Japan Society of Chemotherapy (ibidem) to measure minimum inhibitory concentration (MIC) against 54 strains of clinically isolated methicillin resistant Staphylococcus aureus, from which there were calculated a range of MIC ($MIC_{range}$) of the test compound against these resistant strains, a minimum concentration for inhibiting the growth of the strains by 50% ($MIC_{50}$) and a minimum concentration for inhibiting the growth of the strains by 90% ($MIC_{90}$).

3. Results:

The test results are shown in Table 2.

TABLE 2

| Test compounds | $MIC_{range}$ (μg/ml) | $MIC_{50}$ (μg/ml) | $MIC_{90}$ (μg/ml) |
|---|---|---|---|
| Compound (A) of the invention | 0.025–0.10 | 0.05 | 0.10 |
| Compound (J) of the invention | 0.025–0.10 | 0.05 | 0.10 |
| Known compound (X) | 0.39–1.56 | 0.78 | 1.56 |
| Known compound (Y) | 0.05–0.39 | 0.10 | 0.20 |

Experiment 3 Effect on treatment of general infectious disease

1. Test compounds:
The same as in the Experiment 2.

2. Test microorganisms and inoculum size:
Staphylococcus aureus IID 803 ($5.0 \times 10^7$ CFU/mouse)

*Pseudomonas aeruginosa* E-2 ($3.1 \times 10^4$ CFU/mouse)

3. Method:

The test microorganisms were subjected to standing culture in Trypto-Soya Agar "Nissui" (made by Nissui Seiyaku K.K., Japan) at 37° C. for 16 to 18 hours. The culture was then diluted with PBS (Dulbecco's phosphate buffered saline) and mixed with an equivalent amount of 10% (w/v) Mucin (BACTO MUCIN BACTERIOLOGICAL, made by Difco Co.) to prepare a microorganism solution. The thus prepared microorganism solution (0.5 ml each) was intraperitoneally inoculated to ddY male mice (5 weeks age, weighing 25-28 g, 5 mice in each group), to infect the animals. One hour after the infection, the compound (A) or (J) of the present invention or the known compound (X) suspended in 1% (w/v) aqueous gum arabic or the known compound (Y) dissolved in sterilized distilled water was orally adiministered to mice.

The mice were daily observed for one week, and from the survival number of mice after one week, the 50% effective dose ($ED_{50}$) was calculated by Weil method.

4. Results:

The test results are shown in Table 3.

TABLE 3

| Test microorgs. | $ED_{50}$ (mg/kg) | | | |
|---|---|---|---|---|
| | Compound (A) | Compound (J) | Known comp. (X) | Known comp. (Y) |
| S. aureus IID 803 | 5.8 | 5.8 | 14.0 | 11.7 |
| P. aeruginosa E-2 | 10.2 | 6.8 | 14.0 | 11.7 |

Experiment 4 Effect on treatment of general infectious disease

1. Test compound:

Compound (O): 9,1-(Methylimino)methano-7-fluoro-8-(3,4-dimethyl-1-piperazinyl)-5-oxo-5H-thiazolo[3,2-a]-quinoline-4-carboxylic acid [compound of Example 24]

Compound (P): 9,1-(Methylimino)methano-7-fluoro-8-(3,4,5-trimethyl-1-piperazinyl)-5-oxo-5H-thiazolo[3,2-a]-quinoline-4-carboxylic acid [compound of Example 25]

2. Test microorganism and inoculum size

*Staphylococcus aureus* IID 803 ($2.1 \times 10^7$ CFU/mouse)
*Pseudomonas aeruginosa* E-2 ($3.4 \times 10^4$ CFU/mouse)

3. Method:

The procedure of Experiment 3 was repeated except that ddY male mice weighing 24 to 28 g were employed.

4. Results:

The test results are shown in Table 4.

TABLE 4

| Microorganisms | $ED_{50}$ (mg/kg) | |
|---|---|---|
| | Compound (O) | Compound (P) |
| S. aureus IID 803 | 2.8 | 1.9 |
| P. aeruginosa E-2 | 9.4 | 11.1 |

Experiment 5 Acute toxicity ($LD_{50}$)

1. Method:

The compound (A) or (J) of the present invention was suspended in 1% (w/v) aqueous gum arabic to prepare a suspension in concentration of 100 mg/ml. The suspension was orally administered to ddY male mice (5 weeks age, weighing 20 to 25 g, 5 mice in each group), which had been fasted for 18 hours, at a rate of 2000 mg/kg body weight of the compound (A) or (J). These mice were observed for a dead number for two weeks.

2. Results:

After administration of the compound (A) or (J) of the present invention at a rate of 2000 mg/kg body weight, no death of mice was observed.

Experiment 6 Acute toxicity ($LD_{50}$)

1. Method:

The compound (O) or (P) of the present invention was suspended in sterilized distilled water to prepare a suspension. The suspension was orally adminstered to ddY male mice (5 weeks age, weighing 20 to 25 g, 5 mice in each group), which had been fasted for 18 hours. These mice were observed for a dead number for a week and an acute toxicity ($LD_{50}$) was calculated by Weil method.

2. Results:

The compounds (O) and (P) of the present invention had $LD_{50}$ values of 1414 mg/kg and 1071 mg/kg, respectively.

The preparation of the compound of the present invention is illustrated by means of the following Reference Examples and Examples, but should not be construed to be limited thereto.

REFERENCE EXAMPLE 1

Preparation of diethyl [(2,3,4-trifluoroanilino)(3-chloro-2-oxopropylthio)methylene]malonate [compound (VIII) in which $R^5$ is ethyl]:

Diethyl [(2,3,4-trifluoroanilino)(mercapto)methylene]malonate sodium (3.5 g) (cf. European patent publication No. 286089) was dissolved in N,N-dimethylformamide (15 ml) and thereto was added 1,3-dichloroacetone (1.2 g) and the mixture was stirred at room temperature for 30 minutes. The reaction solution was filtered to remove insoluble substance and the filtrate was dried under reduced pressure. To the residue was then added water and the solution was extracted with chloroform. The extract was washed with a NaCl solution and dried over anhydrous magnesium sulfate and the solvent was distilled off under reduced pressure to give the title compound (4.0 g) as pale yellow oil.

Mass spectrum (m/e): 439 ($M^+$)

REFERENCE EXAMPLE 2

Preparation of diethyl [3-(2,3,4-trifluorophenyl)-4-chloromethyl-3H-thiazol-2-ylidene]malonate [compound (IX) in which $R^5$ is ethyl]:

To diethyl [(2,3,4-trifluoroanilino)(3-chloro-2-oxopropylthio)methylene]malonate (3.0 g) was added conc. sulfuric acid (6 ml) and the mixture was stirred at room temperature for 90 minutes. To the mixture was then added a piece of ice (6 g) and the mixture was stirred for 1 hour. To the mixture was added cooled water and the mixture was extracted with chloroform. The extract was washed with a NaCl solution and dried over anhydrous magnesium sulfate. After distilling off the solvent under reduced pressure, the obtained residue was recyrstallized from ether to give the title compound (1.76 g) as colorless crystals, m.p. 133°-136° C.

Elementary analysis for $C_{17}H_{15}NO_4SF_3Cl$:
Calcd. (%): C,48.40; H,3.58; N,3.32
Found (%): C,48.56; H,3.54; N,3.26

REFERENCE EXAMPLE 3

Preparation of diethyl (5-methyl-6,7-difluoro-1H,4H-thiazolo[3,4-a]quinoxalin-1-ylidene)malonate [compound (X) in which $R^5$ is ethyl]:

Diethyl [3-(2,3,4-trifluorophenyl)-4-chloromethyl-3H-thiazole-2-ylidene]malonate (2.0 g) was dissolved in acetonitrile (20 ml) and thereto was added 40% solution of methylamine in methanol (6 ml). The mixture was stirred at room temperature for 20 minutes and then heated at 50° C. for 100 minutes. After the reaction mixture was evaporated to dryness under reduced pressure, to the residue was added water and the solution was extracted with chloroform. The extract was washed with a NaCl solution, dried over anhydrous magnesium sulfate and the solvent was distilled off under reduced pressure. The obtained residue was recrystallized from a mixed solvent of hexane - ethyl acetate to give the title compound (1.5 g) as pale yellow crystals, m.p. 146°–148° C.

NMR (CDCl$_3$) δ: 1.2 (6H, t, J=7 Hz), 3.1 (3H, d, J=4.5 Hz), 3.9 (4H, q, J=7 Hz), 4.0 (2H, s), 6.5 (1H, t, J=1 Hz), 6.8 (1H, dt, J=8 Hz, J=9 Hz), 7.3 (1H, ddd, J=2 Hz, J=5 Hz, J=9 Hz)

IR (KBr) $\nu_{max}$ cm$^{-1}$: 1700, 1642, 1506, 1426, 1294, 1188, 1082

Elementary analysis for $C_{18}H_{18}N_2O_4SF_2$:
Calcd. (%): C,54.54; H,4.58; N,7.07
Found (%): C,54.45; H,4.61; N,6.89

REFERENCE EXAMPLE 4

Preparation of ethyl 2-(3-chloro-2-oxopropylthio)-6,7,8-trifluoro-4-hydroxyquinoline-3-carboxylate [compound (XII) in which $R^5$ is ethyl]:

To methylene chloride (200 ml) were added ethyl 4-hydroxy-2-cercapto-6,7,8-trifluoroquinoline-3-carboxylate (16 g) (cf. European patent publication No. 286089), triethylamine (8 g) and 1,3-dichloroacetone (6.72 g) and the mixture was stirred under ice-cooling for 1 hour and further at room temperature for 1 hour. After chloroform (400 ml) was added to the reaction solution, the mixture was washed with 0.1 N HCl, water and a NaCl solution in this order, dried over anhydrous magnesium sulfate and the solvent was evaporated to dryness under reduced pressure. The obtained residue was recrystallized from a mixed solvent of chloroform - isopropyl ether to give the title compound (17.5 g) as colorless crystals, m.p. 175°–181° C.

NMR (DMSO-d$_6$) δ: 1.4 (3H, t, J=7 Hz), 4.1 (2H, s), 4.5 (2H, q, J=7 Hz), 4.8 (2H, s), 7.9 (1H, ddd, J=2 Hz, J=8 Hz, J=10 Hz)

IR (KBr) $\nu_{max}$ cm$^{-1}$: 2990, 1739, 1656, 1591, 1513
Elementary analysis for $C_{15}H_{11}NO_4SF_3Cl$:
Calcd. (%): C,45.75; H,2.82; N,3.56
Found (%): C,45.59; H,2.87; N,3.50

REFERENCE EXAMPLE 5

Preparation of ethyl 7,8,9-trifluoro-1-chloromethyl-5-oxo-5H-thiazolo[3,2-a]quinoline-4-carboxylate [compound (XIII) in which $R^5$ is ethyl]:

To concd. sulfuric acid (80 ml) was added ethyl 2-(3-chloro-2-oxopropylthio)-6,7,8-trifluoro-4-hydroxyquinoline-3-carboxylate (17.5 g) prepared in the same manner as in Reference Example 4 and the mixture was stirred at room temperature for 20 hours. After stirring, the reaction solution was poured on a piece of ice and the resulting precipitate was filtered off, washed with water and recrystallized from chloroform - isopropyl ether to give the title compound (14.2 g) as pale yellow crystals, m.p. 158°–160° C.

NMR (DMSO-d$_6$) δ: 1.3 (3H, t, J=7 Hz), 4.3 (2H, q, J=7 Hz), 5.2 (2H, d, J=5 Hz), 7.8 (1H, s), 8.0 (1H, ddd, J=2 Hz, 8 Hz, 10 Hz)

IR (KBr) $\nu_{max}$ cm$^{-1}$: 3094, 1673, 1609, 1522
Elementary analysis for $C_{15}H_9NO_3SF_3Cl$:
Calcd. (%): C,47.95; H,3.41; N,3.73
Found (%): C,47.80; H,3.53; N,3.71

REFERENCE EXAMPLE 6

Preparation of 3-chloro-2-oxopropyl N-(2,3,4-trifluorophenyl)dithiocarbamate [compound (XV)]:

1,3-Dichloroacetone (2.0 g) was added to methylene chloride (100 ml) and thereto was added triethylammonium N-(2,3,4-trifluorophenyl)dithiocarbamate (5.0 g) (c.f. European patent publication No. 286089) while stirring at 2° to 5° C. After stirring for 60 minutes, the mixture was washed with 3N HCl and then with water. The organic layer was dried over anhydrous sodium sulfate and the solvent was distilled off under reduced pressure. The obtained residue was recrystallized from a mixed solvent of hexane - ethyl acetate - ether to give the title compound (4.2 g).

Mass spectrum (m/e): 313 (M$^+$)

REFERENCE EXAMPLE 7

Preparation of 4-chloromethyl-3-(2,3,4-trifluorophenyl)-2(3H)-thiazolethione [compound (XVI)]:

3-Chloro-2-oxopropyl N-(2,3,4-trifluorophenyl)dithiocarbamate (4.0 g) prepared in the same manner as in Reference Example 6 was added to 30% HCl in methanol (15 ml) and the mixture was refluxed for 3 hours. The solvent was distilled off under reduced pressure and to the residue was added cooled water and the solution was extracted with chloroform. The extract was washed with a NaCl solution, dried over anhydrous sodium sulfate and the solvent was distilled off under reduced pressure. The residue was recrystallized from cyclohexane to give the title compound (2.6 g) as pale yellow crystals, m.p. 127°–130° C.

NMR (CDCl$_3$) δ: 4.1 (1H, d, J=13 Hz), 4.2 (1H, d, J=13 Hz), 6.8 (1H, s), 7.2 (2H, m)

IR (KBr) $\nu_{max}$ cm$^{-1}$: 3072, 1516, 1504, 1314, 1260, 1102
Elementary analysis for $C_{10}H_5NS_2F_3Cl$:
Calcd. (%): C,40.61; H,1.70; N,4.74
Found (%): C,40.59; H,1.80; N,4.71

REFERENCE EXAMPLE 8

Preparation of 5-methyl-6,7-difluoro-1H,4H-thiazolo[3,4-a]quinoxaline-1-thione [compound (XVII)]:

4-Chloromethyl-3-(2,3,4-trifluorophenyl)-2(3H)-thiazolethione (2.5 g) prepared in the same manner as in Reference Example 7 was dissolved in acetonitrile (25 ml) and to the solution was added 40% solution of methylamine in methanol (3.3 g) and the mixture was stirred at 50° C. for 16 hours. The reaction mixture was evaporated to dryness under reduced pressure and to the residue was added water and the solution was extracted with chloroform. The extract was washed with a NaCl solution, dried over anhydrous sodium sulfate and the solvent was distilled off under reduced pressure. The obtained residue was recrystallized from a mixed solvent of cyclohexane - ethyl acetate to give the title compound (2.0 g) as pale yellow crystals, m.p. 165°–167° C.

NMR (CDCl$_3$) δ: 3.0 (3H, d, J=2.5 Hz), 4.0 (2H, d, J=1 Hz), 6.4 (1H, t, J=1 Hz), 6.9 (1H, dt, J=8 Hz, J=9 Hz), 9.3 (1H, ddd, J=2.5 Hz, J=5 Hz, J=9.5 Hz)

IR (KBr) ν$_{max}$ cm$^{-1}$: 1502, 1492, 1306, 1290, 1032

Elementary analysis for C$_{11}$H$_8$N$_2$S$_2$F$_2$:
Calcd. (%): C,48.87; H,2.98; N,10.36
Found (%): C,49.04; H,2.95; N,10.41

REFERENCE EXAMPLE 9

Preparation of 5-methyl-6,7-difluoro-1-methylthio-4H-quinoxalino[1,2-c]thiazolium iodide [compound (XVIII) in which R$^5$ is methyl]:

5-Methyl-6,7-difluoro-1H,4H-thiazolo[3,4-a]quinoxaline-1-thione (0.4 g) prepared in the same manner as in Reference Example 8 and methyl iodide (0.4 g) were dissolved in N,N-dimethylformamide (3 ml) and the solution was allowed to stand in a dark place at room temperature for 40 hours. The resulting precipitate was filtered of and washed with acetonitrile and ether in this order to give the title compound (0.5 g) as yellow crystals.

NMR (DMSO-d$_6$) δ: 3.0 (3H, d, J=4.0 Hz), 3.1 (3H, s), 4.4 (2H, s), 7.3 (1H, dt, J=8 Hz, 9.5 Hz), 7.9 (1H, ddd, J=2 Hz, J=5 Hz, J=9.5 Hz), 8.0 (1H, s)

REFERENCE EXAMPLE 10

Preparation of diethyl (5-methyl-6,7-difluoro-1H,4H-thiazolo[3,4-a]quinoxalin-1-ylidene)malonate [compound (X) in which R5 is ethyl]:

Oily sodium hydride [content: about 60 % (w/w)](54 mg) was suspended in tetrahydrofuran (3 ml) and thereto was added dropwise diethyl malonate (0.2 g) at 20° C. and the mixture was stirred for 20 minutes. To the mixture was added 5-methyl-6,7-difluoro-1-methylthio-4H-quinoxalino[1,2-c]thiazolium iodide (0.5 g) prepared in the same manner as in Reference Example 9 at 10° C. and the mixture was stirred at room temperature for 30 minutes. After the reaction mixture was evaporated to dryness under reduced pressure, cooled water was added. The resulting insoluble substance was filtered off, washed with water, dried and then recrystallized from a mixed solvent of hexane - ethyl acetate to give the title compound (0.34 g) as yellow crystals. The compound had physical properties identical to those of diethyl (5-methyl-6,7-difluoro-1H,4H-thiazolo[3,4-a]quinoxalin-1-ylidene)malonate prepared in Reference Example 3.

REFERENCE EXAMPLE 11

Preparation of diethyl (5-methyl-6,7-difluoro-1H, 4H-thiazolo[3,4-a]quinoxalin-1-ylidene)malonate [compound (X) in which R5 is ethyl]:

To 5-methyl-6,7-difluoro-1H,4H-thiazolo[3,4-a]-quinoxaline-1-thione (18 g) prepared in the same manner as in Reference Example 8 was added toluene (110 ml) and trichloromethyl chloroformate (9.74 ml) and the mixture was stirred at 80° C. for 17 hours. The mixture was decanted to give precipitate containing a small amount of toluene and thereto were added acetonitrile (60 ml) and diethyl malonate (12.88 g). After adding triethylamine (14.9 g) under ice-cooling, the mixture was stirred at room temperature for 40 minutes. The reaction mixture was evaporated to dryness under reduced pressure and to the resulting residue was added water and the solution was extracted with chloroform. The extract was dried over anhydrous sodium sulfate and the solvent was distilled off under reduced pressure. The obtained residue was washed with isopropyl ether to give the title compound (24.3 g). The compound had physical properties identical to those of diethyl (5-methyl-6,7-difluoro-1H,4H-thiazolo[3,4-a]quinoxalin-1-ylidene)malonate prepared in Reference Example 3.

EXAMPLE 1

Preparation of ethyl 9,1-(methylimino)methano-7,8-difluoro-5-oxo-5H-thiazolo[3,2-a]quinoline-4-carboxylate [compound (II-2) in which R$^5$ is ethyl]:

A mixture of diethyl (5-methyl-6,7-difluoro-1H,4H-thiazolo[3,4-a]quinoxalin-1-ylidene)malonate (1.2 g, see Reference Example 3) and polyphosphoric acid (10 g) was stirred with heating at 100° C. for 5 hours. Then cooled water was added to the reaction mixture and the mixture was extracted with chloroform. The extract was washed with a NaCl solution and dried over anhydrous magnesium sulfate and the solvent was distilled off under reduced pressure. The resulting residue was recrystallized from a mixed solvent of chloroform - ethanol to give the title compound (0.6 g) as pale yellow crystals, m.p. around 285° C. (dec.).

NMR (DMSO-d$_6$) δ: 1.3 (3H, t, J=7 Hz), 3.2 (3H, d, J=5.5 Hz), 4.3 (2H, q, J=7 Hz), 4.5 (2H, d, J=1 Hz), 7.3 (1H, s), 7.4 (1H, dd, J=7.5 Hz, J=10.5 Hz)

IR (KBr) ν$_{max}$ cm$^{-1}$: 3060, 1708, 1574, 1496, 1478, 1456, 1050

Elementary analysis for C$_{16}$H$_{12}$N$_2$O$_3$SF$_2$:
Calcd. (%): C,54.85; H,3.45; N,8.00
Found (%): C,54.65; H,3.59; N,7.97

EXAMPLE 2

Preparation of 9,1-(methylimino)methano-7,8-difluoro-5-oxo-5H-thiazolo[3,2-a]quinoline-4-carboxylic acid[compound (II-1)]:

To ethyl 9,1-(methylimino)methano-7,8-difluoro-5-oxo-5H-thiazolo[3,2-a]quinoline-4-carboxylate (1.6 g) prepared in the same manner as in Example 1 was added conc. sulfuric acid (18 ml) and the mixture was stirred at 85° C. for 6 hours. To the reaction mixture was added a piece of ice and the resulting precipitate was filtered off and washed with water to give pale yellow powder (1.25 g), which was recrystallized from a mixed solvent of dimethyl sulfoxide - ethanol to give the title compound (1.0 g), m.p. around 262° C. (dec.).

NMR (DMSO-d$_6$) δ: 3.2 (3H, d, J=6 Hz), 4.6 (2H, s), 7.5 (1H, s), 7.6 (1H, dd, J=7 Hz, J=9Hz), 15.6 (1H, bs)

IR (KBr) ν$_{max}$ cm$^{-1}$: 1690, 1552, 1506, 1480, 1472, 1456, 1404

Elementary analysis for C$_{14}$H$_8$N$_2$O$_3$SF$_2$:
Calcd. (%): C,52.17; H,2.50; N,8.69
Found (%) C,52.07; H,2.77; N,8.47

EXAMPLE 3

Preparation of ethyl 9,1-(methylimino)methano-7,8-difluoro-5-oxo-5H-thiazolo[3,2-a]quinoline-4-carboxylate [compound (II-2) in which R$^5$ is ethyl]:

To acetonitrile (250 ml) were added ethyl 7,8,9-trifluoro-1-chloromethyl-5-oxo-5H-thiazolo[3,2-a]quinoline-4-carboxylate (14 g, see Reference Example 5), 40% solution of methylamine in methanol (3.5 g) and triethylamine (4.5 g) and the mixture was stirred at room temperature for 23 hours. The resulting insoluble substance was filtered off, washed with acetonitrile, water and ethanol in this order and recrystallized from a mixed solvent of chloroform - ethanol to give the title compound (8 g). The compound had physical properties identical to those of ethyl 9,1-(methylimino)methano-7,8-difluoro-5-oxo-5H-thiazolo[3,2-a]-quinoline-4-carboxylate prepared in Example 1.

EXAMPLE 4

Preparation of 9,1-(methylimino)methano-7,8-difluoro-5-oxo-5H-thiazolo[3,2-a]quinoline-4-carboxylic acid [compound (II-1)]:

A mixture of diethyl (5-methyl-6,7-difluoro-1H,4H-thiazolo[3,4-a]quinoxalin-1-ylidene)malonate (0.3 g, see Reference Example 10) and polyphosphoric acid (2.5 g) was stirred with heating at 120° C. for 5 hours to produced the cyclization reaction. Then conc. sulfuric acid (2 g) was added to the reaction mixture and the mixture was stirred at 130° C. for 3 hours. To the reaction mixture was added a piece of ice and the resulting precipitate was filtered off, washed with water, dried and recrystallized from a mixed solvent of dimethyl sulfoxide - ethanol to give the title compound (0.2 g). The compound had physical properties identical to those of 9,1-(methylimino)methano-7,8-difluoro-5-oxo-5H-thiazolo[3,2-a]quinoline-4-carboxylic acid prepared in Example 2.

EXAMPLE 5

Preparation of 9,1-(methylimino)methano-7,8-difluoro-5-oxo-5H-thiazolo[3,2-a]quinoline-4-carboxylic acid [compound (II-1)]:

The title compound was prepared by the following procedures (i) and (ii).

(i) Preparation of dipropionyloxy{9,1-(methylimino)-methano-7,8-difluoro-5-oxo-5H-thiazolo[3,2-a]-quinoline-4-carboxy}borane [compound (IV) in which $R^6$ is ethyl]:

A mixture of boric acid (1.1 g) and propionic anhydride (8.0 g) was stirred with heating at 75° to 80° C. for 50 minutes to give a solution of tripropionyloxyborane. Thereto was added ethyl 9,1-(methylimino)methano-7,8-difluoro-5-oxo-5H-thiazolo[3,2-a]quinoline-4-carboxylate (4.0 g, see Example 3) and the mixture was stirred under reflux for 40 minutes. The mixture was allowed to stand to be cooled to room temperature and the formed crystals were filtered off, washed with isopropyl ether and recrystallized from acetonitrile to give the title compound (5.1 g), m.p. around 256° C. (dec.).

NMR (DMSO-$d_6$) w: 0.9 (6H, t, J=7.5 Hz), 2.2 (4H, q, J=7.5 Hz), 3.3 (3H, s), 4.8 (2H, s), 7.6 (1H, dd, J=10 Hz, 7.2 Hz), 8.0 (1H, s)

IR (KBr) $n_{max}$ cm$^{-1}$: 1724, 1702, 1534

Elementary analysis for $C_{20}H_{17}N_2O_7SF_2B$:

Calcd. (%): C,50.23; H,3.58; N,5.86

Found (%): C,50.21; H,3.62; N,5.92

(ii) Preparation of 9,1-(methylimino)methano-7,8-difluoro-5-oxo-5H-thiazolo[3,2-a]quinoline-4-carboxylic acid [compound (II-1)]:

Dipropionyloxy{9,1-(methylimino)methano-7,8-difluoro-5-oxo-5H-thiazolo[3,2-a]quinoline-4-carboxy}borane (0.5 g) prepared in the above procedure (i) was suspended in acetone (2 ml) and thereto was added conc. hydrochloric acid (0.15 ml) and the mixture was stirred at room temperature. The resulting solid was filtered off, washed with water, acetone and isopropyl ether in this order and recrystallized from a mixed solvent of dimethyl sulfoxide - ethanol to give the title compound (0.36 g). The compound had physical properties identical to those of 9,1-(methylimino)methano-7,8-difluoro-5-oxo-5H-thiazolo[3,2-a]quinoline-4-carboxylic acid prepared in Example 2.

EXAMPLE 6

Preparation of 9,1-(methylimino)methano-7,8-difluoro-5-oxo-5H-thizolo[3,2-a]quinoline-4-carboxylic acid [compound (II-1)]:

Diethyl (5-methyl-6,7-difluoro-1H,4H-thiazolo[3,4-a]quinoxaline-1-ylidene)malonate (2.0 g, see Reference Example 10) was added to 30% fuming sulfuric acid (23.6 g) and the mixture was stirred at room temperature for 24 hours. The reaction mixture was poured on a piece of ice and the resulting precipitate was filtered off and washed with water to give the title compound (1.52 g). The compound had physical properties identical to those of 9,1-(methylimino)methano-7,8-difluoro-5-oxo-5H-thiazolo[3,2-a]quinoline-4-carboxylic acid prepared in Example 2.

EXAMPLE 7

Preparation of 9,1-(methylimino)methano-7-fluoro-8-(4-methyl-1-piperazinyl)-5-oxo-5H-thiazolo[3,2-a]quinoline-4-carboxylic acid [compound (I) in which Z is 4-methyl-1piperazinyl] and hydrochloride thereof:

(a) Preparation of 9,1-(methylimino)methano-7-fluoro-8-(4-methyl-1-piperazinyl)-5-oxo-5H-thiazolo [3,2-a]quinoline-4-carboxylic acid:

9,1-(Methylimino)methano-7,8-difluoro-5-oxo-5H-thiazolo[3,2-a]quinoline-4-carboxylic acid (0.3 g) and 1-methylpiperazine (0.47 g) were added to dimethyl sulfoxide (3 ml) and the mixture was stirred at 100° C. for 10 hours. The reaction mixture was concentrated to dryness under reduced pressure and thereto water (30 ml) and acetic acid (5 ml) were added and the mixture was washed with chloroform. The pH of the aqueous phase was adjusted to 7.5 by adding 1N aqueous sodium hydroxide and the resulting solid was filtered off and washed with water and ethanol in this order. After drying, the obtained crude crystals were recrystallized from a mixed solvent of chloroform - ethanol to give the title compound (0.21 g) as pale yellow crystals, m.p. around 257° C. (dec.).

NMR (DMSO-$d_6$+$D_2O$) δ: 2.3 (3H, s), 2.4-2.5 (4H, m), 2.8 (3H, s), 3.3-3.4 (4H, m), 4.4 (2H, s), 7.5 (1H, s), 7.6 (1H, d, J=13 Hz)

IR (KBr) $v_{max}$ cm$^{-1}$: 2928, 1696, 1504, 1462, 798

Elementary analysis for $C_{19}H_{19}N_4O_3SF$:

Calcd. (%): C,56.70; H,4.76; N,13.92

Found (%): C,56.55; H,4.75; N,13.87

(b) Preparation 9,1-(methylimino)methano-7-fluoro-8-(4-methyl-1-piperazinyl)-5-oxo-5H-thiazolo[3,2-a]-quinoline-4-carboxylic acid hydrochloride:

9,1-(Methylimino)methano-7-fluoro-8-(4-methyl-1-piperazinyl)-5-oxo-5H-thiazolo[3,2-a]quinoline-4-carboxylic acid (0.2 g) prepared in the above procedure (a) was dissolved in 30% solution of hydrogen chloride in methanol (30 ml). Thereto was added ether and the mixture was allowed to stand at room temperature and the formed crystals were filtered off and washed with ethanol and ether in this order to give 9,1-(methylimino)methano-7-fluoro-8-(4-methyl-1-piperazinyl)-5-oxo-5H-thiazolo[3,2-a]quinoline-4-carboxylic acid hydrochloride (0.15 g) as yellow crystals, m.p. around 265° C. (dec. with foaming).

NMR ($D_2O$) δ: 2.8 (3H, s), 2.9 (3H, s), 3.2-3.3 (2H, m), 3.5-3.6 (2H, m), 3.7-3.9 (4H, m), 4.5 (2H, s), 7.5 (1H, s), 7.6 (1H, d, J=13 Hz)

IR (KBr) $v_{max}$ cm$^{-1}$: 3420, 1684, 1472

Elementary analysis for $C_{19}H_{20}N_4O_3SFCl·3/2H_2O$:

Calcd. (%): C,48.98; H,4.98; N,12.03

Found (%): C,48.91; H,4.89; N,11.94

EXAMPLE 8

Preparation of 9,1-(methylimino)methano-7-fluoro-8-(1-piperazinyl)-5-oxo-5H-thiazolo[3,2-a]quinoline-4-carboxylic acid [compound (I) in which Z is 1-piperazinyl]:

9,1-(Methylimino)methano-7,8-difluoro-5-oxo-5H-thiazolo[3,2-a]quinoline-4-carboxylic acid (0.3 g) prepared in the same manner as in Example 2 and piperazine hexahydrate (0.61 g) were added to dimethyl sulfoxide (10 ml) and the mixture was stirred at 80° C. for 32 hours. The resulting precipitate was filtered off, washed with water and ethanol in this order and recrystallized from dimethyl sulfoxide to give the title compound (0.1 g) as orange crystals, m.p. around 255° C. (dec.).

NMR (DMSO-$d_6$+$D_2O$) δ: 2.8 (3H, s), 2.8–2.9 (4H, m), 3.3–3.4 (4H, m), 4.4 (2H, s), 7.5 (1H, s), 7.6 (1H, d, J=13 Hz)

IR (KBr) $\nu_{max}$ cm$^{-1}$: 1699, 1612, 1489, 1466
Elementary analysis for $C_{18}H_{17}N_4O_3SF \cdot \frac{1}{2}H_2O$:
Calcd. (%): C,54.40; H,4.57; N,14.10
Found (%): C,54.52; H,4.47; N,14.04

EXAMPLE 9

Preparation of 9,1-(methylimino)methano-7-fluoro-8-(3-methyl-1-piperazinyl)-5-oxo-5H-thiazolo[3,2-a]quinoline-4-carboxylic acid [compound (I) in which Z is 3-methyl-1-piperazinyl]:

9,1-(Methylimino)methano-7,8-difluoro-5-oxo-5H-thiazolo[3,2-a]quinoline-4-carboxylic acid (0.3 g) prepared in the same manner as in Example 2 and 2-methylpiperazine (0.38 g) were added to dimethyl sulfoxide (10 ml) and the mixture was stirred at 80° C. for 40 hours. The reaction mixture was concentrated to dryness under reduced pressure and the formed precipitate was filtered off, washed with dimethyl sulfoxide, water and ethanol in this order and recrystallized from dimethyl sulfoxide to give the title compound (0.03 g) as orange crystals, m.p. around 240° C. (dec.).

NMR (DMSO-$d_6$+$D_2O$) δ: 1.0 (3H, d, J=5 Hz), 2.8 (3H, s), 2.8–3.0 (4H, m), 3.1–3.3 (1H, m), 3.4–3.5 (2H, m), 4.4 (2H, s), 7.5 (1H, s), 7.6 (1H, d, J=13 Hz)

IR (KBr) $\nu_{max}$ cm$^{-1}$: 1702, 1610, 1490, 1461

EXAMPLE 10

Preparation of 9,1-(methylimino)methano-7-fluoro-8-(3,5-dimethyl-1-piperazinyl)-5-oxo-5H-thiazolo[3,2-a]quinoline-4-carboxylic acid [compound (I) in which Z is 3,5-dimethyl-1-piperazinyl]:

9,1-(Methylimino)methano-7,8-difluoro-5-oxo-5H-thiazolo[3,2-a]quinoline-4-carboxylic acid (0.3 g) prepared in the same manner as in Example 2 and 2,6-dimethylpiperazine (0.36 g) were added to dimethyl sulfoxide (10 ml) and the mixture was stirred at 80° C. for 38 hours. The reaction mixture was concentrated to dryness under reduced pressure and to the resulting residue was added water. The pH of the solution was adjusted to 3.0 by adding dilute hydrochloric acid, followed by filtration. The pH of the filtrate was adjusted to 9.0 by adding aqueous sodium hydroxide solution and the formed precipitate was filtered off, washed with water and recrystallized from a mixed solvent of chloroform - ethanol to give the title compound (0.09 g) as yellow crystals, m.p. around 254° C. (dec.).

NMR (DMSO-$d_6$) δ: 1.0 (6H, d, J=6 Hz), 2.6–2.8 (2H, m), 2.7 (3H, s), 2.9–3.0 (2H, m), 3.3–3.5 (2H, m), 4.4 (2H, s), 7.5 (1H, s), 7.6 (1H, d, J=13 Hz)

IR (KBr) $\nu_{max}$ cm$^{-1}$: 1689, 1612, 1595, 1486, 1472
Elementary analysis for $C_{20}H_{21}N_4O_3SF$:
Calcd. (%): C,57.68; H,5.08; N,13.45
Found (%): C,57.66; H,5.10; N,13.38

EXAMPLE 11

Preparation of 9,1-(methylimino)methano-7-fluoro-8-(1-pyrrolidinyl)-5-oxo-5H-thiazolo[3,2-a]quinoline-4-carboxylic acid [compound (I) in which Z is 1-pyrrolidinyl]:

9,1-(Methylimino)methano-7,8-difluoro-5-oxo-5H-thaizolo[3,2-a]quinoline-4-carboxylic acid (0.3 g) prepared in the same manner as in Example 2 and pyrrolidine (0.33 g) were added to dimethyl sulfoxide (3 ml) and the mixture was stirred at 90° C. for 8 hours. The reaction mixture was concentrated to dryness under reduced pressure and the resulting residue was washed with dimethyl sulfoxide, water and ethanol in this order and recrystallized from dimethyl sulfoxide to give the title compound (0.19 g) as pale yellow crystals, m.p. around 275° C. (dec.).

NMR (DMSO-$d_6$) δ: 1.9–2.0 (4H, m), 2.5 (3H, s), 3.6–3.7 (4H, m), 4.4 (2H, s), 7.5 (1H, s), 7.6 (1H, d, J=14 Hz), 16.0 (1H, s)

IR (KBr) $\nu_{max}$ cm$^{-1}$: 1690, 1478, 1454, 1404, 1380
Elementary analysis for $C_{18}H_{16}N_3O_3SF$:
Calcd. (%): C,57.90; H,4.32; N,11.25
Found (%): C,57.66; H,4.42; N,11.12

EXAMPLE 12

Preparation of 9,1-(methylimino)methano-7-fluoro-8-(3-hydroxy-1-pyrrolidinyl)-5-oxo-5H-thiazolo[3,2-a]quinoline-4-carboxylic acid [compound (I) in which Z is 3-hydroxy-1-pyrrolidinyl]:

9,1-(methylimino)methano-7,8-difluoro-5-oxo-5H-thiazolo[3,2-a]quinoline-4-carboxylic acid (0.3 g) prepared in the same manner as in Example 2 and 3-pyrrolidinol (0.4 g) were added to dimethyl sulfoxide (3 ml) and the mixture was stirred with heating at 100° C. for 3 hours. The reaction mixture was concentrated to dryness under reduced pressure and the resulting residue was washed with water and ethanol in this order and recrystallized from dimethyl sulfoxide to give the title compound (0.18 g) as yellow crystals, m.p. around 265° C. (dec.).

NMR (DMSO-$d_6$+$D_2O$) δ: 1.8–2.1 (2H, m), 2.5 (3H, s), 3.3–3.4 (1H, m), 3.5–3.6 (1H, m), 3.8–4.1 (2H, m), 4.3 (1H, d, J=16.5 Hz), 4.4 (1H, s), 4.5 (1H, d, J=16.5 Hz), 7.5 (1H, s), 7.6 (1H, d, J=14 Hz)

IR (KBr) $\nu_{max}$ cm$^1$: 1614, 1480, 1456, 1406
Elementary analysis for $C_{18}H_{16}N_3O_4SF$:
Calcd. (%): C,55.52; H,4.14; N,10.79
Found (%): C,55.27; H,4.25; N,10.65

EXAMPLE 13

Preparation of 9,1-(methylimino)methano-7-fluoro-8-(3-amino-1-pyrrolidinyl)-5-oxo-5H-thiazolo[3,2-a]quinoline-4-carboxylic acid [compound (I) in which Z is 3-amino-1-pyrrolidinyl]:

The title compound was prepared by the following procedures (i) and (ii).

(i) Preparation of 9,1-(methylimino)methano-7-fluoro-8-(3-acetylamino-1-pyrrolidinyl)-5-oxo-5H-thiazolo[3,2-a]quinoline-4-carboxylic acid [compound (VI) in which $R^1$ is hydrogen atom, n is 0 and $R^5$ is methyl]:

9,1-(Methylimino)methano-7,8-difluoro-5-oxo-5H-thiazolo[3,2-a]quinoline-4-carboxylic acid (0.3 g) prepared in the same manner as in Example 2 and 3-acetylaminopyrrolidine (0.6 g) were added to dimethyl sulfoxide (3 ml) and the mixture was stirred with heating at 90° to 95° C. for 4.5 hours. The reaction mixture was concentrated to dryness under reduced pressure and the resulting residue was washed with water and ethanol in this order and recrystallized from a mixed solvent of dimethyl sulfoxide - ethanol to give the title compound (0.2 g), m.p. 160°–162° C.

NMR (DMSO-$d_6$) δ: 1.4–1.5 (1H, m), 1.7 (3H, s), 1.8–2.0 (1H, m), 2.1–2.2 (1H, m), 2.6 (3H, s), 3.6–3.9 (2H, m), 4.0–4.1 (1H, m), 4.3–4.4 (1H, m), 4.5 (2H, s), 7.5 (1H, s), 7.6 (1H, d, J=14 Hz), 8.2 (1H, d, J=6 Hz), 15.6 (1H, bs)

(ii) Preparation of 9,1-(methylimino)methano-7-fluoro-8-(3-amino-1-pyrrolidinyl)-5-oxo-5H-thiazolo[3,2-a]quinoline-4-carboxylic acid:

To 9,1-(methylimino)methano-7-fluoro-8-(3-acetylamino-1-pyrrolidinyl)-5-oxo-5H-thiazolo[3,2-a]quinoline-4-carboxylic acid (0.2 g) prepared in the above procedure (i) was added 10% aqueous sodium hydroxide (10 ml) and the mixture was stirred with heating at 100° C. for 12 hours. The insoluble substance was filtered off and the pH of the filtrate was adjusted to 7 by adding 3N hydrochloric acid. The resulting precipitate was filtered off, washed with water and ethanol in this order and recrystallized from a mixed solvent of ethanol - cyclohexane to give the title compound (0.1 g) as pale yellow crystals, m.p. around 230° C. (dec.).

NMR (DMSO-$d_6$+$D_2O$) δ: 1.7–1.8 (1H, m), 2.0–2.1 (1H, m), 2.5 (3H, s), 3.4–3.5 (1H, m), 3.5–3.9 (4H, m), 4.4 (2H, s), 7.5 (1H, s), 7.6 (1H, d, J=14 Hz)

IR (KBr) $\nu_{max}$ cm$^{-1}$: 3440, 1696, 1494, 1406, 1380

Elementary analysis for $C_{18}H_{17}N_4O_3SF \cdot \frac{1}{2}H_2O$:
Calcd. (%): C,54.40; H,4.56; N,14.09
Found (%): C,54.24; H,4.46; N,14.11

EXAMPLE 14

Preparation of 9,1-(methylimino)methano-7-fluoro-8-morpholino-5-oxo-5H-thiazolo[3,2-a]quinoline-4-carboxylic acid [compound (I) in which Z is morpholino]:

9,1-(Methylimino)methano-7,8-difluoro-5-oxo-5H-thiazolo[3,2-a]quinoline-4-carboxylic acid (0.3 g) prepared in the same manner as in Example 2 and morpholine (0.32 g) were added to dimethyl sulfoxide (10 ml) and the mixture was stirred with heating at 80° C. for 39 hours. The reaction mixture was concentrated to dryness under reduced pressure and the resulting residue was washed with water and recrystallized from a mixed solvent of chloroform - ethanol to give the title compound (0.12 g) as orange crystals, m.p. around 248° C. (dec.).

NMR (DMSO-$d_6$) δ: 2.8 (3H, s), 3.4–3.5 (4H, m), 3.7–3.8 (4H, m), 4.5 (2H, s), 7.6 (1H, s), 7.7 (1H, d, J=13 Hz), 15.9 (1H, s)

IR (KBr) $\nu_{max}$ cm$^{-1}$: 1710, 1612, 1489, 1470

Elementary analysis for $C_{18}H_{16}N_3O_4SF \cdot \frac{1}{4}H_2O$:
Calcd. (%): C,54.88; H,4.22; N,10.67
Found (%) C,54.88; H,4.20; N,10.56

EXAMPLE 15

Preparation of 9,1-(methylimino)methano-7-fluoro-8-(4-ethyl-1-piperazinyl)-5-oxo-5H-thiazolo[3,2-a]quinoline-4-carboxylic acid [compound (I) in which Z is 4-ethyl-1-piperazinyl]:

9,1-(Methylimino)methano-7,8-difluoro-5-oxo-5H-thiazolo[3,2-a]quinoline-4-carboxylic acid (0.50 g) prepared in the same manner as in Example 6, 1-ethylpiperazine (0.19 g) and triethylamine (0.62 g) were added to dimethyl sulfoxide (4 ml) and the mixture was stirred with heating at 90° C. for 4 hours. The reaction mixture was concentrated to dryness under reduced pressure and the resulting solid was washed with water and ethanol in this order and recrystallized from a mixed solvent of chloroform - ethanol to give the title compound (0.49 g) as pale yellow crystals, m.p. around 276° C. (dec.).

NMR (DMSO-$d_6$) δ: 1.05 (3H, t, J=7 Hz), 2.4 (2H, q, J=7 Hz), 2.7 (3H, s), 3.3 (4H, bs), 3.4 (4H, bs), 4.4 (2H, s), 7.5 (1H, s), 7.6 (1H, d, J=13 Hz), 15.7 (1H, s)

IR (KBr) $\nu_{max}$ cm$^{1}$: 3060, 1710, 1615, 1494

Elementary analysis for $C_{20}H_{21}N_4O_3SF$:
Calcd. (%): C,57.68; H,5.08; N,13.45
Found (%): C,57.59; H,5.09; N,13.43

EXAMPLE 16

Preparation of 9,1-(methylimino)methano-7-fluoro-8-(4-hydroxy-1-piperazinyl)-5-oxo-5H-thiazolo[3,2-a]quinoline-b 4-carboxylic acid [compound (I) in which Z is 4-hydroxy-1piperazinyl]:

The title compound was prepared by the following procedures (i) and (ii).

(i) Preparation of diacetoxy{9,1-(methylimino)-methano-7,8-difluoro-5-oxo-5H-thiazolo[3,2-a]quinoline -4-carboxy}borane [compound (IV) in which $R^6$ is methyl]:

A mixture of boric acid (0.27 g) and acetic anhydride (3 g) was stirred with heating at 75° to 80° C. for 50 minutes to give a solution of triacetoxyborane. Thereto was added ethyl 9,1-(methylimino)methano-7,8-difluoro-5-oxo-5H-thiazolo[3,2-a]quinoline-4-carboxylate (1.0 g) prepared in the same manner as in Example 1 and the mixture was stirred with heating at 100° C. for 40 minutes. The reaction mixture was allowed to stand to be cooled to room temperature and the formed crystals were filtered off and washed with isopropyl ether to give the title compound (1.26 g). The compound was recrystallized from acetonitrile and showed the following physical properties.

Melting point: >285° C.

NMR (DMSO-$d_6$) δ: 1.9 (6H, s), 3.3 (3H, d, J=6 Hz), 4.8 (2H, d, J=1Hz), 7.6 (1H, dd, J=7 Hz, 10 Hz), 7.9 (1H, t, J=1Hz)

IR (KBr) $\nu_{max}$ cm$^{-1}$: 1718, 1697

Elementary analysis for $C_{18}H_{13}N_2O_7SF_2B$:
Calcd. (%): C,48.02; H,2.91; N,6.22
Found (%): C,47.92; H,3.02; N,6.21

(ii) Preparation of 9,1-(methylimino)methano-7-fluoro-8-(4-hydroxy-1-piperazinyl)-5-oxo-5H-thiazolo[3,2-a]quinoline-4-carboxylic acid:

Diacetoxy{9,1-(methylimino)methano-7,8-difluoro-5-oxo-5H-thiazolo[3,2-a]quinoline-4-carboxy}borane (1 g) prepared in the above procedure (i) was added to a mixture of dimethyl sulfoxide (10 ml), 4-hydroxypiperazine dihydrochloride (0.78 g) and triethylamine (1.57 g) and the mixture was stirred at room temperature overnight. Dimethyl sulfoxide was distilled off under reduced pressure to give crude diacetoxy{9,1-(methylimino)methano-7-fluoro-8-(4-hydroxy-1-piperazinyl)-5-oxo-5H-thiazolo[3,2-a]quinoline-4-carboxy}borane. Thereto was added water (10 ml) and the pH of the mixture was adjusted to 2 by adding conc. hydrochloric acid and the mixture was stirred for 30 minutes. The formed crystals were filtered off and washed with a small amount of water. Thereto was added water and insoluble substance was removed by filtration and the pH of the filtrate was adjusted to 7.5 by adding 1N sodium hydroxide. The resulting solid was filtered off, washed with water and ethanol in this order and recrystallized from a mixed solvent of chloroform - ethanol to give the title compound (0.25 g), m.p. >285° C.

NMR (DMSO-$d_6$) δ: 2.6 (2H, m), 2.8 (3H, s), 3.1 (2H, m), 3.3 (2H, m), 3.6 (2H, m), 4.4 (2H, s), 7.5 (1H, s), 7.6 (1H, d, J=12.6 Hz), 8.2 (1H, s), 15.8 (1H, bs)

IR (KBr) $\nu_{max}$ cm$^{-1}$: 1690, 1484, 1454

Elementary analysis for $C_{18}H_{17}N_4O_4SF$:
Calcd. (%): C,53.46; H,4.24; N,13.85
Found (%): C,53.20; H,4.34; N,13.63

EXAMPLE 17

Preparation of 9,1-(methylimino)methano-7-fluoro-8-(3-ethylaminomethyl-1-pyrrolidinyl)-5-oxo-5H-thiazolo[3,2-a]quinoline-4-carboxylic acid [compound (I) in which Z is 3-ethylaminomethyl-1-pyrrolidinyl] hydrochloride:

9,1-(Methylimino)methano-7,8-difluoro-5-oxo-5H-thiazolo[3,2-a]quinoline-4-carboxylic acid (0.5 g) prepared in the same manner as in Example 6, 3-ethylaminomethylpyrrolidine dihydrochloride (0.94 g) and triethylamine (1.25 g) were added to dimethyl sulfoxide (5 ml) and the mixture was stirred with heating at 95° C. for 7 hours. The reaction mixture was allowed to stand to be cooled to room temperature and the resulting precipitate was filtered off, washed with dimethyl sulfoxide, ethanol and ether in this order and recrystallized from N,N-dimethylformamide to give the title compound (0.3 g) as pale yellow crystals, m.p. around 254° C. (dec.).

NMR (DMSO-$d_6$+$D_2O$) δ: 1.2–1.3 (3H, bt), 1.7–1.8 (1H, m), 2.1–2.3 (1H, m), 2.5 (3H, s), 2.5–2.7 (1H, m), 2.9–3.2 (4H, m), 3.5–3.9 (4H, m), 4.4–4.6 (2H, m), 7.49 (1H, s), 7.5 (1H, d, J=13 Hz)

IR (KBr) $\nu_{max}$ cm$^{-1}$: 1702, 1620, 1458

Elementary analysis for $C_{21}H_{24}N_4O_3SFCl·H_2O$:
Calcd. (%): C,52.00; H,5.40; N,11.55
Found. (%): C,51.73; H,5.53; N,11.65

EXAMPLE 18

Preparation of 9,1-(methylimino)methano-7-fluoro-8-(3-methylaminomethyl-1-pyrrolidinyl)-5-oxo-5H-thiazolo[3,2-a]quinoline-4-carboxylic acid [compound (I) in which Z is 3-methylaminomethyl-1-pyrrolidinyl] hydrochloride:

9,1-(Methylimino)methano-7,8-difluoro-5-oxo-5H-thiazolo[3,2-a]quinoline-4-carboxylic acid (0.322 g) prepared in the same manner as in Example 6, 3-methylaminomethylpyrrolidine dihydrochloride (0.57 g) and triethylamine (0.81 g) were added to dimethyl sulfoxide (3 ml) and the mixture was stirred with heating at 95° C. for 8 hours. The reaction mixture was allowed to stand to be cooled to room temperature and the resulting precipitate was filtered off, washed with dimethyl sulfoxide, ethanol and ether in this order and recrystallized from N,N-dimethylformamide to give the title compound (0.26 g) as pale yellow crystals, m.p. around 250° C. (dec.).

NMR (DMSO-$d_6$+$D_2O$) δ: 1.7–1.8 (1H, m), 2.2–2.3 (1H, m), 2.5 (3H, s), 2.5–2.6 (1H, m), 2.6 (3H, s), 3.1 (2H, d, J=7.1Hz), 3.5–3.6 (1H, m), 3.6–3.8 (3H, m), 4.4 (1H, d, J=16.6 Hz), 4.5 (1H, d, J=16.6 Hz), 7.5 (1H, s), 7.5 (1H, d, J=14 Hz)

IR (KBr) $\nu_{max}$ cm$^{-1}$:1684, 1616, 1498

Elementary analysis for $C_{20}H_{22}N_4O_3SFCl·3/2H_2O$:
Calcd. (%): C,50.05; H,5.25; N,11.67
Found (%): C,50.01; H,5.23; N,11.89

EXAMPLE 19

Preparation of 9,1-(methylimino)methano-7-fluoro-8-(4-ethyl-1-piperazinyl)-5-oxo-5H-thiazolo[3,2-a]quinoline-4-carboxylic acid [compound (I) in which Z is 4-ethyl-1-piperazinyl] hydrochloride:

Diacetoxy{9,1-(methylimino)methano-7,8-difluoro-5-oxo-5H-thiazolo[3,2-a]quinoline-4-carboxy}borane [2 g, see Example 16-(i)] was added to a mixture of dimethyl sulfoxide (10 ml), 4-ethylpiperazine (0.6 g) and triethylamine (2 g) and the mixture was stirred at room temperature overnight. Dimethyl sulfoxide was distilled off under reduced pressure to give crude diacetoxy{9,1-(methylimino)methano-7-fluoro-8-(4-ethyl-1-piperazinyl)-5-oxo-5H-thiazolo 3,2-a]quinoline-4-carboxy}borane. Thereto was added water (10 ml) and the pH of the mixture was adjusted to 1 by adding conc. hydrochloric acid and the mixture was stirred for 30 minutes. The formed crystals were filtered off, washed with a small amount of water and recrystallized from water to give the title compound (1.1 g), m.p.>295° C.

NMR ($D_2O$) δ: 1.4 (3H, t, J=7.3 Hz), 2.8 (3H, s), 3.2–3.4 (4H, m), 3.6–3.9 (6H, m), 4.4 (2H, s), 6.8 (1H, d, J=12.2 Hz), 7.4 (1H, s)

IR (KBr) $\nu_{max}$ cm$^{-1}$: 1690, 1464, 1390

Elementary analysis for $C_{20}H_{22}N_4O_3SFCl·3/2H_2O$:
Calcd. (%): C,50.05; H,5.25; N,11.67
Found. (%): C,50.21; H,5.09; N,11.72

EXAMPLE 20

Preparation of 9,1-(methylimino)methano-7-fluoro-8-(4-methyl-1-piperazinyl)-5-oxo-5H-thiazolo[3,2-a]quinoline-4-carboxylic acid [compound (I) in which Z is 4-methyl-1-piperazinyl]:

The title compound was prepared by the following procedures (i) and (ii).

(i) Preparation of ethyl 9,1-(methylimino)methano-7-fluoro-8-(4-methyl-1-piperazinyl)-5-oxo-5H-thiazolo[3,2-a]quinoline-4-carboxylate:

Ethyl 9,1-(methylimino)methano-7,8-difluoro-5-oxo-5H-thiazolo[3,2-a]quinoline-4-carboxylate (1.0 g, see Example 1) and 1-methylpiperazine (1.42 g) were added to dimethyl sulfoxide (10 ml) and the mixture was stirred with heating at 95° C. for 82 hours. The reaction mixture was concentrated to dryness under reduced pressure and to the resulting residue was added water and the mixture was extracted with chloroform. The chloroform layer was washed with water, dried over anhydrous magnesium sulfate and then concentrated to dryness under reduced pressure. The obtained residue was recrystallized from a mixed solvent of cyclohexane - ethyl acetate to give the title compound (0.8 g) as pale yellow crystals, m.p. around 244° C. (dec.).

NMR (CDC$l_3$) ν: 1.5 (3H, t, J=7 Hz), 2.4 (3H, s), 2.6 (4H, m), 2.8 (3H, s), 3.4 (4H, m), 4.2 (2H, s), 4.5 (2H, q, J=7 Hz), 6.8 (1H, s), 7.8 (1H, d, J=13 Hz)

IR (KBr) $\nu_{max}$ cm$^{-1}$ 1710, 1566, 1464

Elementary analysis for $C_{21}H_{23}N_4O_3SF$:
Calcd. (%): C,58.59; H,5.39; N,13.02
Found (%): C,58.33; H,5.41; N,12.88

(ii) Preparation of 9,1-(methylimino)methano-7-fluoro-8-(4-methyl-1-piperazinyl)-5-oxo-5H-thiazolo [3,2-a]quinoline-4-carboxylic acid:

Ethyl 9,1-(methylimino)methano-7-fluoro-8-(4-methyl-1-piperazinyl)-5-oxo-5H-thiazolo[3,2-a]quinoline-4- carboxylate (0.5 g) prepared in the above procedure (i) and 1N sodium hydroxide (2.6 ml) were added to ethanol (130 ml) and the mixture was refluxed for 5 hours. The reaction mixture was concentrated to dryness under reduced pressure and to the residue were added water.(80 ml) and acetic acid (2 ml) and insoluble substance was removed by filtration. The pH of the filtrate was adjusted to 8 by adding 1N sodium hydroxide and the filtrate was extracted with a mixed solvent of chloroform - methanol (10:1). The extract was concentrated to dryness under reduced pressure and the residue was washed with water, dried and recrystallized from a mixed solvent of chloroform - ethanol to give the title compound (0.27 g) as pale yellow crystals. The compound had physical properties identical to those of 9,1-(methylimino)- methano-7 fluoro-8-(4-methyl-1-piperazinyl)-5-oxo-5H-thiazolo[3,2-a]quinoline-4-carboxylic acid prepared in Example 7-(a).

EXAMPLE 21

Preparation of 9,1-(methylimino)methano-7-fluoro-8-(4-methyl-1-piperazinyl)-5-oxo-5H-thiazolo[3,2-a]quinoline-4-carboxylic acid [compound (I) in which Z is 4-methyl-1-piperazinyl] hydrochloride:

The title compound was prepared by the following procedures (i) and (ii).

(i) Preparation of dipropionyloxy{9,1-(methylimino)-methano-7-fluoro-8-(4-methyl-1-piperazinyl)-5-oxo-5H-thiazolo[3,2-a]quinoline-4-carboxy}borane [compound (V) in which Z is 4-methyl-1-piperazinyl and $R^6$ is ethyl]:

A mixture of dipropionyloxy{9,1-(methylimino)methano-7,8-difluoro-5-oxo-5H-thiazolo[3,2-a]quinoline-4-carboxy}borane (3.0 g, see Example 5-(i)], dimethyl sulfoxide (10 ml) and 4-methylpiperazine (1.89 g) was stirred at room temperature for 15.5 hours. The formed crystals were filtered off, washed with dimethyl sulfoxide and acetonitrile in this order and recrystallized from acetonitrile to give the title compound (3.2 g), m.p. around 228° C. (dec.).

NMR (DMSO-$d_6$) δ: 0.9 (6H, t, J=7.5 Hz), 2.2 (4H, q, J=7.5 Hz), 2.3 (3H, s), 2.8 (3H, s), 3.3 (4H, bs), 3.5 (4H, bs), 4.6 (2H, s), 7.7 (1H, d, J=12.5 Hz), 7.9 (1H, s)

IR (KBr) $\nu_{max}$ cm$^{-1}$: 1718, 1688, 1516

Elementary analysis for $C_{25}H_{28}N_4O_7SFB$:
Calcd. (%): C,53.77; H,5.05; N,10.03
Found (%): C,53.70; H,5.02; N,10.06

(ii) Preparation of 9,1-(methylimino)methano-7-fluoro-8-(4-methyl-1-piperazinyl)-5-oxo-5H-thiazolo[3,2-a]quinoline-4-carboxylic acid hydrochloride:

Dipropionyloxy{9,1-(methylimino)methano-7-fluoro-8-(4-methyl-1-piperazinyl)-5-oxo-5H-thiazolo[3,2-a]quinoline-4-carboxy}borane (3.0 g) prepared in the above procedure (i) was added to water (10 ml) and the pH of the mixture was adjusted to 1 with conc. hydrochloric acid and the mixture was stirred at room temperature for 40 minutes. The formed crystals were filtered off, washed with water and recrystallized from water to give the title compound (1.7 g). The compound had physical properties identical to those of 9,1-(methylimino)methano-7-fluoro-8-(4-methyl-1-piperazinyl)-5-oxo-5H-thiazolo[3,2-a]quinoline-4-carboxylic acid hydrochloride prepared in Example 7-(b).

EXAMPLE 22

Preparation of 9,1-(methylimino)methano-7-fluoro-8(4-methyl-1-piperazinyl)-5-oxo-5H-thiazolo[3,2-a]quinoline-4-carboxylic acid [compound (I) in which Z is 4-methyl-1piperazinyl] p-toluenesulfonate:

9,1-(Methylimino)methano-7-fluoro-8-(4-methyl-1-piperazinyl)-5-oxo-5H-thiazolo[3,2-a]quinoline-4-carboxylic acid hydrochloride (6.3 g) prepared in the same manner as in Example 21 was suspended in water (100 ml) and the pH of the suspension was adjusted to 7.5 with 10% aqueous solution of sodium hydroxide. Insoluble substance was filtered off, washed with water and suspended in a solution of p-toluenesulfonate monohydrate (4.7 g) in ethanol (100 ml). To the suspension were added water (200 ml) and ethanol (200 ml) and the mixture was refluxed for 1 hour and then allowed to stand at room temperature. The formed crystals were filtered off and washed with water to give the title compound (6.3 g) as white crystals, m.p. around 300° C. (dec.).

NMR (DMSO-$d_6$) δ: 2.3 (3H, s), 2.8 (3H, s), 2.9 (3H, s), 3.3–3.5 (8H, m), 4.5 (2H, s), 7.1 (2H, d, J=8 Hz), 7.5 (2H, d, J=8 Hz), 7.6 (1H, s), 7.7 (1H, d, J=12 Hz), 9.3–10.1 (1H, bs), 15.8 (1H, s)

IR (KBr) $\nu_{max}$ cm$^{-1}$: 3120, 3000, 2844, 2712, 2640, 1696, 1616, 1598, 1472, 1442, 1400, 1236, 1160

Elementary analysis for $C_{26}H_{27}N_4O_6S_2F$:
Calcd. (%): C,54.34; H,4.74; N,9.75
Found (%): C,54.23; H,4.73; N,9.63

EXAMPLE 23

Preparation of 9,1-(methylimino)methano-7-fluoro-8-(4-ethyl-1-piperazinyl)-5-oxo-5H-thiazolo[3,2-a]quinoline-4-carboxylic acid [compound (I) in which Z is 4-ethyl-1piperazinyl] p-toluenesulfonate:

9,1-(Methylimino)methano-7-fluoro-8-(4-ethyl-1-piperazinyl)-5-oxo-5H-thiazolo[3,2-a]quinoline-4-carboxylic acid hydrochloride (3.9 g) prepared in the same manner as in Example 19 was added to water (60 ml) and the mixture was warmed to 75° C. to dissolve the compound. Then sodium p-toluenesulfonate (2.5 g) dissolved in water (10 ml) was added and the mixture was allowed to stand at room temperature. The formed crystals were filtered off and washed with water to give the title compound (4.2 g) as pale yellow crystals, m.p. around 295° C. (dec.).

NMR (DMSO-$d_6$) δ: 1.3 (3H, t, J=7 Hz), 2.3 (3H, s), 2.8 (3H, s), 3.1–3.9 (8H, m), 4.5 (2H, s), 7.1 (2H, d, J=8 Hz), 7.5 (2H, d, J=8 Hz), 7.6 (1H, s), 7.7 (1H, d, J=12.5 Hz), 9.3–9.5 (1H, bs), 15.8 (1H, s)

IR (KBr) $\nu_{max}$ cm$^{-1}$: 1689, 1612, 1583, 1520, 1501, 1465, 1451, 1221

Elementary analysis for $C_{27}H_{29}N_4O_6S_2F \cdot H_2O$:
Calcd. (%): C,54.67; H,5.01; N,9.45
Found (%): C,54.64; H,4.99; N,9.39

EXAMPLE 24

Preparation of 9,1-(methylimino)methano-7-fluoro-8-(3,4-dimethyl-1-piperazinyl)-5-oxo-5H-thiazolo [3,2-a]quinoline-4-carboxylic acid [compound (I) in which Z is 3,4-dimethyl-1-piperazinyl]:

The title compound was prepared by the following procedures (i) and (ii).

(i) Preparation of 9,1-(methylimino)methano-7-fluoro-8-(3-methyl-1-piperazinyl)-5-oxo-5H-thiazolo 3,2-a]quinoline-4-carboxylic acid [compound (I) in which Z is 3-methyl-1-piperazinyl] hydrochloride:

A mixture of diacetoxy{9,1-(methylimino)methano-7,8-difluoro-5-oxo-5H-thiazolo[3,2-a]quinoline-4-carboxy}-borane [7.0.g, see Example 16-(i)], dimethyl sulfoxide (8 ml) and 2-methylpiperazine (3.7 g) was stirred with heating at 80° C. for 4 hours. The formed crystals were filtered off and washed with acetonitrile. The crystals were added to ice-water (100 g) and thereto was added conc. hydrochloric acid (8 ml) and the mixture was stirred at room temperature for 1.5 hours, followed by filtrating off the crystals. The crystals were added to water (50 ml) and the mixture was warmed to 70° C. to dissolve the crystals, followed by filtration. To the filtrate was added conc. hydrochloric acid (1 ml) and the mixture was allowed to stand at room temperature. The formed crystals were filtered off and washed with cooled water to give the title compound (4.3 g) as pale yellow crystals, m.p. around 284° C. (dec.).

NMR (D$_2$O) δ: 1.4 (3H, d, J=6 Hz), 2.7 (3H, s), 3.2–3.8 (7H, m), 4.3 (2H, s), 6.6 (1H, d, J=12 Hz), 7.3 (1H, s)

IR (KBr) $\nu_{max}$ cm$^{-1}$: 1690, 1615, 1462

Elementary analysis for C$_{19}$H$_{20}$N$_4$O$_3$SFCl:

Calcd. (%): C,51.99; H,4.59; N,12.76

Found (%): C,51.95; H,4.59; N,12.68

(ii) Preparation of 9,1-(methylimino)methano-7-fluoro-8-(3,4-dimethyl-1-piperazinyl)-5-oxo-5H-thiazolo[3,2-a]quinoline-4-carboxylic acid:

A mixture of 9,1-(methylimino)methano-7-fluoro-8-(3-methyl-1-piperazinyl)-5-oxo-5H-thiazolo[3,2-a]quinoline-4-carboxylic acid hydrochloride (3.0 g) prepared in the above procedure (i), sodium formate (0.93 g), formic acid (15 ml) and formalin (15 ml) was stirred with heating at 80° C. for 14 hours. The reaction mixture was added to ice-water and the pH of the mixture was adjusted to 9.0 with aqueous sodium hydroxide. The formed crystals were filtered off and dissolved in a mixed solvent of chloroform - methanol (4:1) and solution was washed with water, followed by distilling off the solvent. The obtained residue was recrystallized from ethanol to give the title compound (0.92 g) as pale yellow crystals, m.p. around 244° C. (dec.).

NMR (DMSO-d$_6$) δ: 1.0 (3H, d, J=6 Hz), 2.1–2.4 (2H, m), 2.2 (3H, s), 2.7 (3H, s), 2.7–3.0 (2H, m), 3.2–3.5 (3H, m), 4.5 (2H, s), 7.5 (1H, s), 7.6 (1H, d, J=12.5 Hz), 15.9 (1H, s)

IR (KBr) $\nu_{max}$ cm$^{-1}$: 1692, 1613, 1490, 1460

Elementary analysis for C$_{20}$H$_{21}$N$_4$O$_3$SF:

Calcd. (%): C,57.68; H,5.08; N,13.45

Found (%): C,57.58; H,5.06; N,13.36

EXAMPLE 25

Preparation of 9,1-(methylimino)methano-7-fluoro-8-(3,4,5-trimethyl-1-piperazinyl)-5-oxo-5H-thiazolo[3,2-a]-quinoline-4-carboxylic acid [compound (I) in which Z is 3,4,5-trimethyl-1-piperazinyl]:

The title compound was prepared by the following procedures (i) and (ii).

(i) Preparation of 9,1-(methylimino)methano-7-fluoro-8-(3,5-dimethyl-1-piperazinyl)-5-oxo-5H-thiazolo[3,2-a]quinoline-4-carboxylic acid [compound (I) in which Z is 3,5-dimethyl-1-piperazinyl] hydrochloride:

A mixture of diacetoxy{9,1-(methylimino)methano-7,8-difluoro-5-oxo-5H-thiazolo[3,2-a]quinoline-4-carboxy}-borane 7.0 g, see Example 16-(i)], dimethyl sulfoxide (8 ml) and 2,6-dimethylpiperazine (3.9 g) was stirred with heating at 80° C. for 4 hours. The formed crystals were filtered off and washed with acetone. The crystals were added to ice-water (100 g) and thereto was added conc. hydrochloric acid (7 ml) and the mixture was stirred at room temperature for 1 hour, followed by filtrating off the crystals. The crystals were added to water (950 ml) and the mixture was warmed to 90° C. to dissolve the crystals, followed by filtration of the solution. To the filtrate was added conc. hydrochloric acid (2 ml) and the mixture was allowed to stand at room temperature. The formed crystals were filtered off and washed with cooled water to give the title compound (4.4 g) as pale yellow crystals, m.p. around 295° C. (dec.).

NMR (D$_2$O) δ: 1.4 (6H, d, J=6 Hz), 2.8 (3H, s), 3.2–3.4 (2H, m), 3.6–3.8 (4H, m), 4.4 (2H, s), 6.8 (1H, d, J=12 Hz), 7.4 (1H, s)

IR (KBr) $\nu_{max}$ cm$^{-1}$: 1690, 1615, 1463

Elementary analysis for C$_{20}$H$_{22}$N$_4$O$_3$SFCl:

Calcd. (%): C,53.04; H,4.90; N,12.37

Found (%): C,53.04; H,4.89; N,12.36

(ii) Preparation of 9,1-(methylimino)methano-7-fluoro-8-(3,4,5-trimethyl-1-piperazinyl)-5-oxo-5H-thiazolo[3,2-a]quinoline-4-carboxylic acid:

9,1-(Methylimino)methano-7-fluoro-8-(3,5-dimethyl-1-piperazinyl)-5-oxo-5H-thiazolo[3,2-a]quinoline-4-carboxylic acid hydrochloride (2.5 g) prepared in the above procedure (i) was dissolved in water (about 500 ml) with heating. The pH of the solution was adjusted to 9.0 by adding aqueous sodium hydroxide. The formed crystals were filtered off and washed with water to give 9,1-(methyl-imino)methano-7-fluoro-8-(3,5-dimethyl-1-piperazinyl)-5-oxo-5H-thiazolo[3,2-a]quinoline-4-carboxylic acid (2.1 g, the same compound as prepared in Example 10). This compound (0.5 g), methyl iodide (0.43 g) and potassium carbonate (0.5 g) were added to N,N-dimethylformamide (20 ml) and the mixture was stirred at room temperature for 23 hours. The reaction mixture was added to water and the pH of the mixture was adjusted to 9.5 with dilute hydrochloric acid, followed by extraction with a mixed solvent of chloroform - methanol (10:1). The extract was washed with water and concentrated to dryness under reduced pressure. To the reside were added 5% aqueous potassium hydroxide solution (6 ml), water (18 ml) and ethanol (12 ml) and the mixture was refluxed for 15 minutes. The reaction mixture was added to water and the pH of the solution was adjusted to 9.5 with dilute hydrochloric acid, followed by extraction with a mixed solvent of chloroform - methanol (4:1). The extract was washed with water, concentrated to dryness under reduced pressure and the residue was recrystallized from a mixed solvent of acetonitrile - ethanol to give the title compound (0.08 g) as pale yellow crystals, m.p. around 250° C. (dec.).

NMR (DMSO-d$_6$) δ: 1.0 (6H, d, J=6 Hz), 2.2 (3H, s), 2.2–2.4 (2H, m), 2.7 (3H, s), 2.9–3.1 (2H, m), 3.4–3.5 (2H, m), 4.5 (2H, s), 7.5 (1H, s), 7.6 (1H, d, J=12.5 Hz), 15.9 (1H, s)

IR (KBr) $\nu_{max}$ cm$^{-1}$: 1688, 1612, 1502, 1463

Elementary analysis for C$_{21}$H$_{23}$N$_4$O$_3$SF:

Calcd. (%): C,58.59; H,5.39; N,13.01

Found (%): C,58.60; H,5.39; N,12.96

EXAMPLE 26

Preparation of tablets:

Tablets each containing 100 mg of 9,1-(methylimino)methano-7-fluoro-8-(4-methyl-1-piperazinyl)-5-oxo-5H-thiazolo[3,2-a]quinoline-4-carboxylic acid [compound prepared in Example 7-(a)] were prepared as follows:

(Formula)

| Ingredients | Part by weight |
|---|---|
| The active ingredient (Compound prepared in Example 7-(a) | 100 |
| Corn starch | 46 |
| Microcrystalline cellulose | 98 |
| Hydroxypropyl cellulose | 2 |
| Magnesium stearate | 4 |

(Procedure)

To a mixture of the active ingredient, corn starch and microcrystalline cellulose was added a solution of hydroxypropyl cellulose in water (50 parts by weight) and the mixture was kneaded well. The kneaded mixture was passed through a mesh to produce granules. After drying the granules, magnesium stearate was mixed with the granules and the mixture was tabletted by a conventional method to give tablets (each 250 mg).

EXAMPLE 27

Preparation of granules:

Granules each containing 9,1-(methylimino)methano-7-fluoro-8-(4-methyl-1-piperazinyl)-5-oxo-5H-thiazolo[3,2-a]quinoline-4-carboxylic acid [compound prepared in Example 7-(a)](200 mg) per 500 mg granules were prepared as follows:

(Formula)

| Ingredients | Part by weight |
|---|---|
| The active ingredient (compound prepared in Example 7-(a) | 200 |
| Lactose | 185 |
| Corn starch | 109 |
| Hydroxypropyl cellulose | 6 |

(Procedure)

To a mixture of the active ingredient, lactose and corn starch was added a solution of hydroxypropyl cellulose in water (120 parts by weight) and the mixture was kneaded well. The kneeded mixture was passed through a No. 20 mesh sieve to produce granules. The granules were dried and passed through a sieve of desired size to yield the granules.

EXAMPLE 28

Preparation of capsules:

Capsules each containing 100 mg of 9,1-(methylimino)methano-7-fluoro-8-(4-methyl-1-piperazinyl)-5-oxo-5H-thiazolo[3,2-a]quinoline-4-carboxylic acid [compound prepared in Example 7-(a)] were prepared as follows:

(Formula)

| Ingredients | Part by weight |
|---|---|
| The active ingredient [compound prepared in Example 7-(a)] | 100 |
| Lactose | 35 |
| Corn starch | 60 |
| Magnesium stearate | 5 |

(Procedure)

All the above ingredients were mixed throughly and the resulting powdery mixture was packed into gelatin capsules in each amount of 200 mg.

EXAMPLES 29–31

Preparation of tablets:

Tablets each containing 100 mg of 9,1-(methylimino)methano-7-fluoro-8-(4-methyl-1-piperazinyl)-5-oxo-5H-thiazolo[3,2-a]quinoline-4-carboxylic acid hydrochloride [compound prepared in Example 7-(b)], 9,1-(methylimino)-methano-7-fluoro-8-(4-ethyl-1-piperazinyl)-5-oxo-5H-thiazolo[3,2-a]quinoline-4-carboxylic acid [compound prepared in Example 15], or 9,1-(methylimino)methano-7-fluoro-8-(4-ethyl-1-piperazinyl)-5-oxo-5H-thiazolo [3,2-a]quinoline-4-carboxylic acid hydrochloride (compound prepared in Example 19) were prepared by the procedure as described in Example 26 except that the compound of Example 7-(b), 15 or 19 was employed in place of the compound prepared in Example 7-(a) as the active ingredient.

EXAMPLES 32–33

Preparation of granules:

Granules each containing 9,1-(methylimino)methano-7-fluoro-8-(4-methyl-1-piperazinyl)-5-oxo-5H-thiazolo[3,2-a]quinoline-4-carboxylic acid hydrochloride [compound prepared in Example 7-(b)]or 9,1-(methylimino)methano-7-fluoro-8-(4-ethyl-1-piperazinyl)-5-oxo-5H-thiazolo[3,2-a]quinoline-4-carboxylic acid hydrochloride [compound prepared in Example 19]were prepared by the procedure as described in Example 27 except that the compound of Examples 7-(b) or 19 was employed in place of the compound prepared in Example 7-(a) as the active ingredient.

EXAMPLES 34–35

Preparation of capsules:

Capsules each containing 100 mg of 9,1-(methylimino)methano-7-fluoro-8-(4-methyl-1-piperazinyl)-5-oxo-5H-thiazolo[3,2-a]quinoline-4-carboxylic acid hydrochloride [compound prepared in Example 7-(b)]or 9,1-(methylimino)-methano-7-fluoro-8-(4-ethyl-1-piperazinyl)-5-oxo-5H-thiazolo[3,2-a]quinoline-4-carboxylic acid (compound prepared in Example 15) were prepared by the procedure as described in Example 28 except that the compound of Example 7-(b) or 15 were employed in place of the compound prepared in Example 7-(a) as the active ingredient.

What is claimed is:

1. A quinolinecaboxylic acid derivative represented by the formula (I):

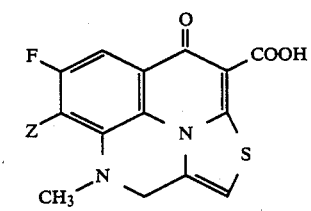

wherein Z is

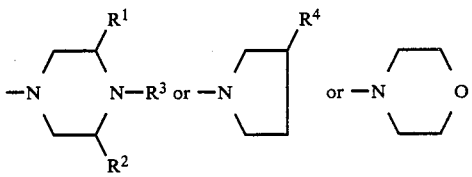

in which R¹ and R² are each hydrogen atom or a lower alkyl, R³ is hydrogen atom, hydroxy or a lower alkyl and R⁴ is hydrogen atom, hydroxy, amino, aminomethyl, a (lower alkyl)aminomethyl or a di(lower alkyl)aminomethyl, or a pharmaceutically acceptable salt thereof.

2. The compound according to claim 1, wherein Z is

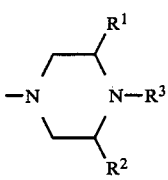

(where R¹ and R² are each hydrogen atom or a $C_{1-2}$ alkyl, and R³ is hydrogen atom, hydroxy or a $C_{1-2}$ alkyl),

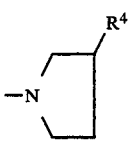

(where R⁴ is hydrogen atom, hydroxy, amino, a ($C_{1-2}$ alkyl)aminomethyl, or a di($C_{1-2}$ alkyl)aminomethyl, or

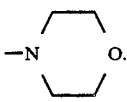

3. The compound according to claim 1 wherein Z is

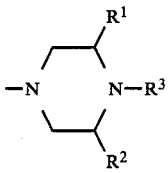

(where R¹ and R² are each hydrogen atom or methyl, and R³ is hydrogen atom, hydroxy, methyl or ethyl),

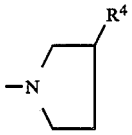

(where R⁴ is hydrogen atom, hydroxy, amino, methylaminomethyl, or ethylaminomethyl), or

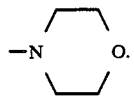

4. The compound according to claim 1, wherein Z is a member selected from the group consisting of 1-piperazinyl, 4-methyl-1-piperazinyl, 4-ethyl-1-piperazinyl, 3,5-di-metyl-1-piperazinyl, 3-methyl-1-piperazinyl, 4-ethyl-1-piperazinyl, 3,5-dimethyl-1-piperazinyl, 3-methyl-1-piperazinyl, 3,4-dimethyl-1-piperazinyl, 3,4,5-trimethyl-1-piperazinyl, 4-hydroxy-1-piperazinyl, 1-pyrrolidinyl, 3-hydroxy-1-pyrrolidinyl, 3-methylaminomethyl-1-pyrrolidinyl, 3-dimethylaminomethyl-1-pyrrolidinyl, 3-ethylaminomethyl-1-pyrrolidinyl and morpholino.

5. The compound according to claim 1, which is a member selected from the following compounds:
   9,1-(Methylimino)methano-7-fluoro-8-(4-methyl-1-piperazinyl)-5-oxo-5H-thiazolo[3,2-a]quinoline-4-carboxylic acid, or a pharmaceutically acceptable salt thereof;
   9,1-(Methylimino)methano-7-fluoro-8-(1-piperazinyl)-5-oxo-5H-thiazolo[3,2-a]quinoline-4-carboxylic acid, or a pharmaceutically acceptable salt thereof;
   9,1-(Methylimino)methano-7-fluoro-8-(3-methyl-1-piperazinyl)-5-oxo-5H-thiazolo[3,2-a] quinoline-4-carboxylic acid, or a pharmaceutically acceptable salt thereof;
   9,1-(Methylimino)methano-7-fluoro-8-(3,5-dimethyl-1-piperazinyl)-5-oxo-5H-thiazolo[3,2-a]quinoline-4-carboxylic acid, or a pharmaceutically acceptable salt thereof;
   9,1-(Methylimino)methano-7-fluoro-8-(1-pyrrolidinyl)-5-oxo-5H-thiazolo[3,2-a]quinoline-4-carboxylic acid, or a pharmaceutically acceptable salt thereof;
   9,1-(Methylimino)methano-7-fluoro-8-(3-hydroxy-1-pyrrolidinyl)-5-oxo-5H-thiazolo[3,2-a]quinoline-4-carboxylic acid, or a pharmaceutically acceptable salt thereof;
   9,1-(Methylimino)methano-7-fluoro-8-(3-amino-1-pyrrolidinyl)-5-oxo-5H-thiazolo[3,2-a]quinoline-4-carboxylic acid, or a pharmaceutically acceptable salt thereof;
   9,1-(Methylimino)methano-7-fluoro-8-morpholino-5-oxo-5H-thiazolo[3,2-a]quinoline-4-carboxylic acid, or a pharmaceutically acceptable salt thereof;
   9,1-(Methylimino)methano-7-fluoro-8-(4-ethyl-1-piperazinyl)-5-oxo-5H-thiazolo[3,2-a]quinoline-4-carboxylic acid, or a pharmaceutically acceptable salt thereof;
   9,1-(Methylimino)methano-7-fluoro-8-(4-hydroxy-1-piperazinyl)-5-oxo-5H-thiazolo[3,2-a]quinoline-4-carboxylic acid, or a pharmaceutically acceptable salt thereof;
   ],1-(Methylimino)methano-7-fluoro-8-(3-ethylaminomethyl-1-pyrrolidinyl)-5-oxo-5H-thiazolo[3,2-a]quinoline-4-carboxylic acid, or a pharmaceutically acceptable salt thereof;
   9,1-(Methylimino)methano-7-fluoro-8-(3-methylamino-methyl-1-pyrrolidinyl)-5-oxo-5H-thiazolo[3,2-a]quinoline-4-carboxylic acid, or a pharmaceutically acceptable salt thereof;

9,1-(Methylimino)methano-7-fluoro-8-(3,4-dimethyl-piperazinyl)-5-oxo-5H-thiazolo[3,2-a]quinoline-4-carboxylic acid, or a pharmaceutically acceptable salt thereof;

9,1-(Methylimino)methano-7-fluoro-8-(3,4,5-trimethyl-1-piperazinyl)-5-oxo-5H-thiazolo[-3,2-a[quinoline-4-carboxylic acid, or a pharmaceutically acceptable salt thereof.

6. An antibacterial composition comprising as an active ingredient an effective amount of a quinolinecarboxylic acid derivative reresented by the formula (I):

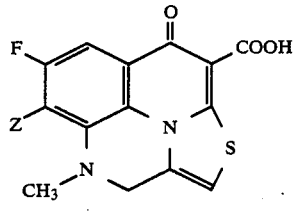
(I)

wherein Z is

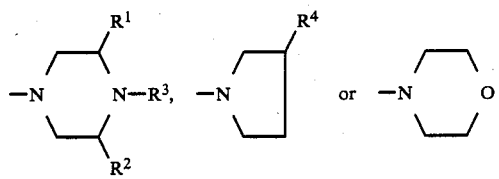

in which $R^1$ and $R^2$ are each hydrogen atom or a lower alkyl, $R^3$ is hydrogen atom, hydroxy or a lower alkyl and $R^4$ is hydrogen atom, hydroxy, amino, aminomethyl, a (lower alkyl)aminomethyl or a di(lower alkyl)aminomethyl, or a pharmaceutically acceptable salt thereof, in admixture with a conventional pharmaceutically acceptable carrier or diluent.

* * * * *

UNITED STATES PATENT AND TRADEMARK OFFICE
CERTIFICATE OF CORRECTION

PATENT NO. : 4,971,967

DATED : November 20, 1990

INVENTOR(S) : KONDO et al.

It is certified that error appears in the above-identified patent and that said Letters Patent is hereby corrected as shown below:

Col. 9, line 34; the symbol --(X)-- should appear below the fourth compound in the process (a).

Col. 17, line 53; "de][1,4-benzoxazine" should read --de][1,4]benzoxazine--.

Col. 21, line 36; "2-cercapto" should read --2-mercapto--.

Col. 23, line 19; "filtered of" should read --filtered off--.

Col. 23, line 29; "R5" should read --$R^5$--.

Col. 23, line 52; "R5" should read --$R^5$--.

Col. 25, line 33; "carboxy]borane" should read --carboxy}borane--.

Col. 26, line 22; "-lpiperazinyl" should read -- -1-piperazinyl--.

Col. 28, line 50; "$cm^1$" should read --$cm^{-1}$--.

Col. 30, line 14; "$cm^1$" should read --$cm^{-1}$--.

Col. 30, line 22; "quinoline-b4-" should read --quinoline-4- --.

Col. 30, line 23; "-lpiperazinyl" should read -- -1-piperazinyl--.

Col. 31, line 35; "$+D_{20}$" should read --$+D_2O$--.

Col. 32, line 18; "thiazolo 3,2-a]" should read --thiazolo [3,2-a]--.

Col. 32, line 57; "$(CDC_{13})$γ:" should read --$(CDCl_3)$δ:--.

UNITED STATES PATENT AND TRADEMARK OFFICE
CERTIFICATE OF CORRECTION

PATENT NO. : 4,971,967

DATED : November 20, 1990

INVENTOR(S) : KONDO et al.

It is certified that error appears in the above-identified patent and that said Letters Patent is hereby corrected as shown below:

Col. 33, line 16; "9,1-(methylimino)-methano-7" should read --9,1-(methylimino)methano-7--.

Col. 33, line 68; "8(4-methyl" should read --8-(4-methyl--.

Col. 34, line 2; "-1piperazinyl" should read -- -1-piperazinyl--.

Col. 34, line 32; "-1piperazinyl" should read -- -1-piperazinyl--.

Col. 34, line 50; "·H$_2$O" should read --·1/4H$_2$O--.

Col. 34, from line 62 to 63; "thiazolo 3,2-a" should read --thiazolo [3,2-a].

Col. 34, line 67; "boxy}-borane" should read --boxy}borane--.

Col. 35, line 61; "boxy}-borane" should read --boxy}borane--.

Col. 36, line 27; "9,1-(methyl-imino)" should read --9,1-(methylimino)--.

Col. 37, line 46; "kneeded mixture" should read --kneaded mixture--.

Col. 38, line 14; "(methylimino)-methano" should read -(methylimino)methano-.

Col. 38, line 47; "(methylimino)-methano" should read -(methylinino)methano-.

Col. 40; lines 11 to 12; delete "3,5-di-metyl-1-piperazinyl,3-methyl-1-piperazinyl,4-ethyl-1-piperazinyl,".

Col. 40, line 15; after "3-hydroxy-1-pyrrolidinyl", insert --3-amino-1-pyrrolidinyl, 3-aminomethyl-1-pyrrolidinyl,--.

Col. 40, line 61; "],1-(Methylimino)" should read --9,1-(Methylimino)--.

UNITED STATES PATENT AND TRADEMARK OFFICE
CERTIFICATE OF CORRECTION

PATENT NO. : 4,971,967

DATED : November 20, 1990

INVENTOR(S) : KONDO et al.

It is certified that error appears in the above-identified patent and that said Letters Patent is hereby corrected as shown below:

Col. 40, line 66; "methylamino-methyl" should read --methylaminomethyl--.

Col. 41, line 5; "piperazinyl" should read --1-piperazinyl--.

Col. 41, from line 17 to 18; "thiazolo [-3,2-a[quinoline" should read --thiazolo [3,2-a]quinoline--.

Signed and Sealed this

Twenty-fifth Day of August, 1992

Attest:

DOUGLAS B. COMER

Attesting Officer

Acting Commissioner of Patents and Trademarks